United States Patent
Goncalves et al.

(10) Patent No.: US 10,188,696 B2
(45) Date of Patent: Jan. 29, 2019

(54) PHARMACEUTICAL COMPOSITIONS

(71) Applicants: Elisabete Goncalves, Basel (CH); Karin Rapp, Basel (CH); Bertrand Sutter, Hesingue (FR); Frank Stowasser, Mürg (DE); Bjoern Trupp, Kandern-Feuerbach (DE); Sebastian Chabaut, Thonon-les-bains (FR); Julien Thorens, St Blaise (FR)

(72) Inventors: Elisabete Goncalves, Basel (CH); Karin Rapp, Basel (CH); Bertrand Sutter, Hesingue (FR); Frank Stowasser, Mürg (DE); Bjoern Trupp, Kandern-Feuerbach (DE); Sebastian Chabaut, Thonon-les-bains (FR); Julien Thorens, St Blaise (FR)

(73) Assignees: Novartis AG, Basel (CH); Debiopharma S.A., Lausanne (CH)

(*) Notice: Subject to any disclaimer, the term of this patent is extended or adjusted under 35 U.S.C. 154(b) by 0 days.

(21) Appl. No.: 15/153,035

(22) Filed: May 12, 2016

(65) Prior Publication Data
US 2016/0367624 A1 Dec. 22, 2016

Related U.S. Application Data

(63) Continuation of application No. 13/992,948, filed as application No. PCT/EP2011/072463 on Dec. 12, 2011, now abandoned.

(60) Provisional application No. 61/422,499, filed on Dec. 13, 2010.

(30) Foreign Application Priority Data

Feb. 18, 2011 (WO) .................. PCT/IB2011/000319
Mar. 25, 2011 (WO) .................. PCT/IB2011/000653

(51) Int. Cl.
A61K 38/13 (2006.01)
A61K 9/48 (2006.01)
A61K 9/00 (2006.01)
A61K 9/107 (2006.01)
A61K 47/10 (2017.01)
A61K 47/14 (2017.01)
A61K 47/22 (2006.01)
A61K 47/26 (2006.01)

(52) U.S. Cl.
CPC ............ *A61K 38/13* (2013.01); *A61K 9/0053* (2013.01); *A61K 9/0095* (2013.01); *A61K 9/107* (2013.01); *A61K 9/1075* (2013.01); *A61K 9/4858* (2013.01); *A61K 47/10* (2013.01); *A61K 47/14* (2013.01); *A61K 47/22* (2013.01); *A61K 47/26* (2013.01)

(58) Field of Classification Search
None
See application file for complete search history.

(56) References Cited

U.S. PATENT DOCUMENTS

| 6,096,338 A | 8/2000 | Lacy et al. |
| 2003/0143250 A1 | 7/2003 | Hauer et al. |
| 2004/0121944 A1 | 6/2004 | Legora et al. |

FOREIGN PATENT DOCUMENTS

| EP | 1250125 A2 | 10/2002 |
| EP | 1354582 A2 | 10/2003 |
| GB | 2257359 | 1/1993 |
| WO | 199702042 A1 | 1/1997 |
| WO | WO99/56727 A2 | 11/1999 |
| WO | 00/01715 | 1/2000 |
| WO | 0048571 A1 | 8/2000 |
| WO | 2006/038088 | 4/2006 |
| WO | 2006094829 A1 | 9/2006 |
| WO | 2010052559 A1 | 5/2010 |
| WO | WO2012/080176 A2 | 6/2012 |

OTHER PUBLICATIONS

New Hope Network (http://www.newhope.com/news/understanding-benefits-and-basics-soft-gel-encapsulation May 13, 2009).*
Flisiak et al., "The Cuyclophilin Inhibitor Debio-025 Shows Potent Anti-Hepatitits C Effect in Patients Coinfected with Hepatitits C and Human Immunodeficiency Virus", Hepatology, vol. 47, No. 3, pp. 817-826 (2008).
Campas et al., DEBIO-025 Drugs of the Future, vol. 33, No. 12, pp. 1012-1017 (2008).
Coelmont L., et al: "DEB025 (Alisporivir) Inhibits Hepatitis C Virus Replication by Preventing a Cyclophilin A Induced Cis-Trans Isomerisation in Domain II of NSSA"; PloS One; vol. 5, pp. 1-14, dated Oct. 27, 2010.
Fischer G., et al: "Cyclophilin inhibitors for the treatment of HCV infection"; Thomson Reuters; vol. 11, pp. 911-918 of 2010.
Gallay, PA; Lin K. (Feb. 15, 2013). "Profile of alisporivir and its potential in the treatment of hepatitis C.". Drug Des Devel Ther. 7: 105-115.
Coelmont L, Kaptein S, Paeshuyse J, et al. (Dec. 2008). "Debio 025, a cyclophilin binding molecule, is highly efficient in clearing HCV replicon containing cells, alone or when combined with Specifically Targeted Antiviral Therapy or HCV (STAT-C) inhibitors". Antimicrob. Agents Chemother. 53 (3): 967-76.
Paeshuyse J, Kaul A, De Clercq E, et al. (Apr. 2006). "The non-immunosuppressive cyclosporin DEBIO-025 is a potent inhibitor of hepatitis C virus replication in vitro". Hepatology 43 (4): 761-70. doi:10.1002/hep.21102. PMID 16557546.
Ptak RG, Gallay PA, Jochmans D, et al. (Apr. 2008). "Inhibition of human immunodeficiency virus type 1 replication in human cells by Debio-025, a novel cyclophilin binding agent". Antimicrob. Agents Chemother. 52 (4): 1302-17. doi:10.1128/AAC.01324-07.
Reutenauer J, et al. (Oct. 2008). "Investigation of Debio 025, a cyclophilin inhibitor, in the dystrophic mdx mouse, a model for Duchenne muscular dystrophy". Br. J. Pharmacol. 155 (4): 574-84.
Eastman Vitamin E (TPGS) Application and Properties (createdOct. 14, 2005, modifiedJan. 21, 2009).

* cited by examiner

Primary Examiner — James H Alstrum-Acevedo
Assistant Examiner — Tara L Martinez
(74) Attorney, Agent, or Firm — David Kurlandsky

(57) ABSTRACT

The invention provides lipid-based pharmaceutical compositions comprising alisporivir.

10 Claims, 4 Drawing Sheets

PHARMACEUTICAL COMPOSITIONS

The present invention relates to lipid-based compositions, specifically to lipid-/surfactant-based compositions for oral administration of cyclophilin binding non-immunosuppressive cyclosporins, in particular, compositions having alisporivir as an active agent.

PCT/EP 2004/009804, WO 2005/021028, or WO 2006/071619 disclose non-immunosuppressive cyclosporins which bind to cyclophilin and which have also been found to have an inhibitory effect on Hepatitis C virus (HCV). Alisporivir (Debio-025) is a cyclophilin (Cyp) inhibitor and its mode of action as an anti-HCV agent is via inhibition of host proteins, in particular of cyclophilin A, that are directly involved in HCV replication.

Cyclosporins are sparingly soluble in water and, therefore, are difficult to formulate into commercially acceptable formulations. Microemulsion preconcentrates, as lipid-/surfactant-based formulations consisting of a hydrophilic phase, a lipophilic phase and poorly-water soluble drugs, such as cyclosporin A have been described, for example, in the UK patent application No 2 222 770 A (equivalent to DE-A-39 30 928).

The provision of dosage forms which can contain cyclosporins in sufficiently high concentration to permit convenient use and to achieve proper exposure in humans represents an additional difficulty in formulating cyclosporins. Moreover, supersaturated formulations are usually undesirable due to their unpredictable stabilities.

SUMMARY OF THE DISCLOSURE

Surprisingly, it is seen that, depending on the formulation, water content varying from 2% to 15% by weight of the composition is required in order to develop thermodynamically stable, non-supersaturated formulations of alisporivir with a high drug load of about 15 to about 20% by weight of the composition.

In accordance with the present invention, a particularly stable pre-concentrate has been found. Specifically, lipid-/surfactant-based pharmaceutical compositions with poorly-water soluble drugs, such as alisporivir, having a high drug load of about 15 to about 20% by weight of the composition, are obtained using water content from about 2% to about 15% by weight of the composition. In contrast to the teaching of the art, such compositions can, in practice, be prepared comprising water as an essential component.

The present invention provides a lipid-/surfactant-based pharmaceutical composition comprising alisporivir, a carrier medium comprising a lipophilic component, a surfactant, a hydrophilic component and water.

Alisporivir may be in amorphous or crystalline form and can include any pharmaceutically acceptable salts or esters thereof.

The pharmaceutical compositions of the present invention are preferably for oral administration but may be suitable for buccal, pulmonal, topical, rectal or vaginal administration.

In a further aspect of the present invention, a pre-concentrate, such as lipid-/surfactant-based formulation comprises alisporivir, a lipophilic component, a surfactant, a hydrophilic component and water is disclosed.

The pharmaceutical composition in the form of a pre-concentrate, such as lipid-/surfactant-based formulation contains the active agent, as herein defined and is capable of producing colloidal structures when diluted with an aqueous medium, for example water, or gastric juices. The colloidal structures are preferably liquid droplets wherein the liquid droplets are in the emulsion size range or in the microemulsion size range.

In another aspect, the present invention provides a pharmaceutical composition comprising alisporivir for administration to a subject in need thereof, wherein the pharmaceutical composition is in the form of a pre-concentrate, such as lipid-/surfactant-based formulation.

In a further aspect, the present invention provides an emulsion or a microemulsion comprising alisporivir as the active agent, a carrier medium that comprises a lipophilic component, a surfactant, a hydrophilic component and water.

The colloidal structures of the microemulsion or emulsion form spontaneously or substantially spontaneously when the components of the composition of the invention are brought into contact with an aqueous medium, e.g. by simple shaking by hand for a short period of time, for example for 10 seconds. The compositions of the invention are kinetically stable, e.g. for at least 15 minutes or up to 4 hours, or even to 24 hours or longer.

DETAILED DESCRIPTION OF THE DISCLOSURE

Figure 1:
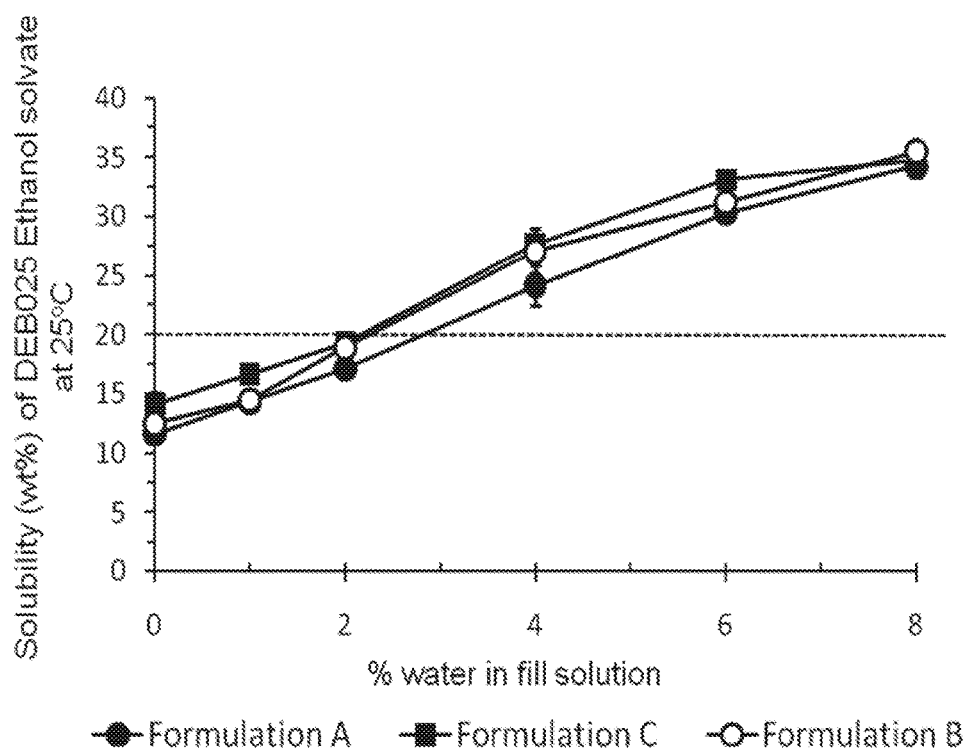
FIG. 1 is a graph which illustrates the impact of water in the equilibrium solubility at 25° C. of DEB025 Ethanol solvate in vitamin E TPGS-based formulations.

The lipophilic component comprises one or more lipophilic substances. The hydrophilic component comprises one or more hydrophilic substances. The surfactant comprises one or more surfactants.

The compositions of the invention may include a variety of additives including antioxidants, antimicrobial agents, enzyme inhibitors, stabilizers, preservatives, flavours, sweeteners and further components such as those described in Fiedler, H. P. "Lexikon der Hilfsstoffe für Pharmazie, Kosmetik and angrenzende Gebiete", Editio Cantor, D-7960 Aulendorf, 5$^{th}$ revised and expanded edition (2002). These additives will conveniently be dissolved in the carrier medium.

In another aspect, the present invention provides a pharmaceutical composition, preferably in form of a pre-concentrate, such as lipid-/surfactant-based formulation for oral administration, comprising:
1) alisporivir in an amount of about 15% to about 20% by weight of the composition,
2) a lipophilic component,
3) a surfactant,
4) a hydrophilic component, and
5) water in an amount of about 2% to about 15% by weight of the composition, preferably of about 4% to about 10% by weight of the composition.

The lipophilic component is selected from the group consisting of glyceryl mono-C6-C14-fatty acid esters, mixtures of mono- and di-glycerides of C6-C18 fatty acids, glyceryl di-C6-C18-fatty acid esters, medium chain fatty acid triglyceride, glyceryl mono-C16-C18-fatty acid esters, mixed mono-, di-, tri-glycerides, acetylated monoglycerides (C18), propylene glycol monofatty acid esters, propylene glycol mono- and di-fatty acid esters, propylene glycol diesters, propylene glycol monoacetate and propylene glycol diacetate, transesterified ethoxylated vegetable oils, sorbitan fatty acid esters, esterified compounds of fatty acid and primary alcohols, glycerol triacetate or (1,2,3)-triacetin, acetyl triethyl citrate, tributylcitrate or acetyl tributyl citrate, polyglycerol fatty acid esters, PEG-fatty alcohol ether, fatty alcohols and fatty acids, tocopherol and its derivatives (e.g. acetate), pharmaceutically acceptable oils, alkylene polyol ethers or esters, hydrocarbons, ethylene glycol esters, pentaerythriol fatty acid esters and polyalkylene glycol ethers The surfactant is selected from the group consisting of reaction products of a natural or hydrogenated castor oil and ethylene oxide, polyoxyethylene-sorbitan-fatty acid esters, polyoxyethylene fatty acid esters, polyoxyethylene-polyoxypropylene co-polymers and block co-polymers or poloxamers, polyoxyethylene mono esters of a saturated C10 to C22, polyoxyethylene alkyl ethers, sodium alkyl sulfates and sulfonates, and sodium alkyl aryl sulfonates, water soluble tocopheryl polyethylene glycol succinic acid esters (TPGS), polyglycerol fatty acid esters, alkylene polyol ethers or esters, polyethylene glycol glyceryl fatty acid esters, sterols and derivatives thereof, transesterified, polyoxyethylated caprylic-capric acid glycerides, sugar fatty acid esters, PEG sterol ethers, dioctylsodiumsulfosuccinate, phospholipids, salts of fatty acids, fatty acid sulfates and sulfonates, salts of acylated amino acids, medium or long-chain alkyl, e.g. C6-C18, ammonium salts.

The hydrophilic component is selected from the group consisting of polyethylene glycol glyceryl $C_6$-$C_{10}$ fatty acid esters, N-alkylpyrrolidone, benzyl alcohol, triethyl citrate, polyethylene glycols, ethanol, transcutol ($C_2H_5$—[O—($CH_2$)$_2$]$_2$—OH), glycofurol (also known as tetrahydrofurfuryl alcohol polyethylene glycol ether), 1,2-propylene glycol, dimethylisosorbide (Arlasolve), triethylenglycol, ethylacetate, glycerol, sorbitol and ethyl lactate.

The hydrophilic component can also be but does not have to be a solvent for the drug substance. Hydrophilic components with an amphiphilic nature can function as co-surfactants, although they are not usually regarded as surfactants, due to their ability to further reduce the surface tension below the level achieved with the surfactants. Typically, hydrophilic components which are also co-surfactants for alisporivir include for instance ethanol, glycerol or sorbitol, preferably ethanol or glycerol.

In another aspect, the present invention provides a pharmaceutical composition as defined above and wherein the water in an amount of about 4 to about 5% by weight of the composition.

In yet another aspect, the present invention provides a pharmaceutical composition comprising alisporivir in an amount of about 19% to about 20% by weight of the composition and the water is in an amount of about 4% to about 5% by weight of the composition.

In yet another aspect, the present invention provides a pharmaceutical composition comprising alisporivir in an amount of about 19% to about 20% by weight of the composition, water in an amount of about 2% to about 15%, preferably of about 2% to about 5%, by weight of the composition and a hydrophilic component in an amount of about 5% to about 25%, preferably suitable hydrophilic components include for instance ethanol and/or polyethylene glycol.

In another aspect, the present invention provides a pharmaceutical composition, preferably in form of a pre-concentrate such as lipid-/surfactant-based formulation, for oral administration comprising:
1) alisporivir in an amount of about 15% to about 20% by weight of the composition,
2) a lipophilic component,
3) a surfactant,
4) a polyethylene glycol, and
5) water in an amount of about 2% to about 10% by weight of the composition.

In another aspect, the present invention provides a pharmaceutical composition, preferably in form of a pre-concentrate, such as lipid-/surfactant-based formulation, for oral administration comprising:
1) alisporivir in an amount of about 15% to about 20% by weight of the composition,
2) a lipophilic component,
3) a surfactant,
4) a hydrophilic component and a polyethylene glycol, and
5) water in an amount of about 2% to about 10% by weight of the composition.

In another aspect, the present invention provides a pharmaceutical composition, preferably in form of a pre-concentrate, such as lipid-/surfactant-based formulation, for oral administration comprising:
1) alisporivir in an amount of about 19% to about 20% by weight of the composition,
2) a lipophilic component,
3) a surfactant,
4) ethanol, and
5) water in an amount of about 4% to about 5% by weight of the composition.

The compositions of the present invention include a hydrophilic component or phase.

Suitable hydrophilic compounds or components include:
1) Polyethylene glycol glyceryl $C_6$-$C_{10}$ fatty acid esters
    The fatty acid ester may include mono and/or di and/or tri fatty acid esters. It optionally includes both saturated and unsaturated fatty acids having a chain length of from e.g. $C_8$-$C_{10}$. The polyethylene glycols may have e.g. from 5 to 10 [$CH_2$—$CH_2$—O] units, e.g. 7 units. A particularly suitable fatty acid ester is polyethylene glycol (7) glyceryl monococoate, which is commercially available, e.g. under the trade name Cetiol® HE, e.g. from Henkel KGaA. Cetiol® HE has a D. (20°) of 1.05, an acid value of less than 5, a saponification value of about 95, a hydroxyl value of about 180 and an iodine value of less than 5 (H. Fiedler, loc. cit., vol 1, page 410) or Lipestrol E-810.
2) N-alkylpyrrolidone
    Particularly suitable is, e.g. N-Methyl-2-pyrrolidone, e.g. as commercially available under the trade name Pharmasolve™, from e.g. International Specialty Products (ISP). N-methylpyrrolidone exhibits the following additional characterising data: molecular weight 99.1, $D.^{25}$ 1.027-1.028, purity (as area % by GC) (including Methyl Isomers) 99.85% min (H. Fiedler, loc. cit., vol 2, page 1303, manufacturer information).
3) Benzyl alcohol
    This is commercially available from e.g. Merck or may be obtained by distillation of benzyl chloride with potassium or sodium carbonate. Benzyl alcohol exhibits the following additional characterising data: molecular weight 108.14, D. 1.043-1.049, $n_D$ 1.538-1.541. (H. Fiedler, loc. cit., vol 1, page 301; Handbook of Pharmaceutical Excipients, $3^{rd}$ edition loc. cit., page 41).

4) Triethyl citrate

Can be obtained esterifying citric acid and ethanol. Triethyl citrate is commercially available, e.g. under the trade names Citroflex® 2, or in a pharmaceutical grade under the name TEC-PG/N, from e.g. Morflex Inc. Particularly suitable is triethyl citrate which has molecular weight of 276.3, a specific gravity of 1.135-1.139, a refractive index of 1.439-1.441, a viscosity (25°) of 35.2 mPa s, assay (anhydrous basis) 99.0-100.5%, water max. 0.25% (Fiedler, H. P., loc. cit., vol 1, page 446; "Handbook of Pharmaceutical Excipients", loc. cit., page 573).

5) Polyethylene glycols e.g. Polyethylene glycol 400 (PEG400), polyethylene glycol 300 (PEG300).

6) Ethanol

Other suitable hydrophilic compounds include transcutol ($C_2H_5$—[O—$(CH_2)_2]_2$—OH), glycofurol (also known as tetrahydrofurfuryl alcohol polyethylene glycol ether), 1,2-propylene glycol, dimethylisosorbide (Arlasolve), triethylenglycol, ethylacetate, and ethyllactate.

The hydrophilic component may comprise 5 to 60% by weight of the composition of the invention, e.g. 10 to 50%; preferably 10 to 40% by weight, more preferably about 10 to about 30% by weight, most preferred about 20% by weight.

The hydrophilic component may comprise one component or a mixture of two or more hydrophilic components. The ratio of main hydrophilic component to hydrophilic co-component is typically from about 0.5:1 to about 2:1.

The compositions of the invention include a lipophilic component or phase. The lipophilic component is preferably characterized by a low HLB value of less than 10, e.g. up to 8.

Suitable lipophilic components include:

1) Glyceryl mono-$C_6$-$C_{14}$-fatty acid esters

These may be obtained by esterifying glycerol with vegetable oil followed by molecular distillation. Monoglycerides suitable for use in the compositions of the invention include both symmetric (i.e. β-monoglycerides) as well as asymmetric monoglycerides (α-monoglycerides. They also include both uniform glycerides (in which the fatty acid constituent is composed primarily of a single fatty acid) as well as mixed glycerides (i.e. in which the fatty acid constituent is composed of various fatty acids) The fatty acid constituent may include both saturated and unsaturated fatty acids having a chain length of from e.g. $C_8$-$C_{14}$. Particularly suitable are caprylic or lauric acid monoglycerides which are commercially available, e.g. under the trade names Imwitor® 308 or Imwitor® 312, respectively, from e.g. sasol. For example Imwitor® 308 comprises at least 80% monoglycerides and exhibits the following additional characterising data: free glycerol max 6%, acid value max. 3, saponification value 245-265, iodine value max. 1, water content max. 1%. Typically it comprises 1% free glycerol, 90% monoglycerides, 7% diglycerides, 1% triglycerides (H. Fiedler, loc. cit., volume 1, page 906). A further example is Capmul MCM C8 from Abitec Corporation.

2) Mixtures of mono- and di-glycerides of $C_6$-$C_{18}$ fatty acids

These may include both symmetric (i.e. β-monoglycerides and α,α¹-diglycerides) as well as asymmetric mono- and di-glycerides (i.e. α-monoglycerides and α,β-diglycerides) and acetylated derivatives thereof. They also include both uniform glycerides (in which the fatty acid constituent is composed primarily of a single fatty acid) as well as mixed glycerides (i.e. in which the fatty acid constituent is composed of various fatty acids) and any derivatives thereof with lactic or citric acid. The fatty acid constituent may include both saturated and unsaturated fatty acids having a chain length of from e.g. $C_8$-$C_{10}$. Particularly suitable are mixed caprylic and capric acid mono- and di-glycerides as commercially available, e.g. under the trade name Imwitor® 742 or Imwitor 928, from e.g. Sasol. For example Imwitor® 742 comprises at least 45% monoglycerides and exhibits the following additional characterising data: free glycerol max. 2%, acid value max. 2, saponification value 250-280, iodine value max. 1, water max. 2% (H. Fiedler, loc. cit., vol 1, page 906). Other suitable mixtures comprise mono/diglycerides of caprylic/capric acid in glycerol as known and commercially available under e.g. the trade name Capmul® MCM from e.g. Abitec Corporation. Capmul® MCM exhibits the following additional characterising data: acid value 2.5 max., alpha-Mono (as oleate) 80% min., free glycerol 2.5% max., iodine value 1 max., chain length distribution: caproic acid (C6) 3% max., caprylic acid (C8) 75% min., capric acid (C10) 10% min., lauric acid (C12) 1.5% max., moisture (by Karl Fisher) 0.5% max. (manufacturer information). Suitable examples of mono-/di-glcyerides with additional derivatization with lactic or citric acid are those marketed under the brand names of Imwitor 375, 377 or 380 by sasol. Furthermore, the fatty acid constituent may include both saturated and unsaturated fatty acids having a chain length of from e.g. $C_{16}$-$C_{18}$. A suitable example is Tegin® 0 (glyceryl oleate) exhibiting the following additional characterising data: monoglyceride content 55-65%, peroxide value max. 10, water content max. 1%, acid value max. 2, iodine value 70-76, saponification value 158-175, free glycerol max. 2%, (manufacturer information).

3) Glyceryl di-$C_6$-$C_{18}$-fatty acid esters

These may include symmetric (i.e. α,α¹-diglycerides) and asymmetric diglycerides (i.e. α,β-diglycerides) and acetylated derivatives thereof. They also include both uniform glycerides (in which the fatty acid constituent is composed primarily of a single fatty acid) as well as mixed glycerides (i.e. in which the fatty acid constituent is composed of various fatty acids) and any acetylated derivatives thereof. The fatty acid constituent can include both saturated and unsaturated fatty acids having a chain length of from $C_6$-$C_{18}$, e.g. $C_6$-$C_{16}$, e.g. $C_8$-$C_{10}$, e.g. $C_8$. Particularly suitable is caprylic diglycerides, which is commercially available, e.g. under the trade name Sunfat® GDC-S, e.g. from Taiyo Kagaku Co., Ltd. Sunfat® GDC-S has an acid value of about 0.3, a diglyceride content of about 78.8%, and a monoester content of about 8.9.

4) Medium chain fatty acid triglyceride

These may include triglycerides of saturated fatty acid having 6 to 12, e.g. 8 to 10, carbon atoms. Suitable medium chain fatty acid triglycerides are those known and commercially available under the trade names Acomed®, Myritol®, Captex®, Neobee® M 5 F, Miglyol®810, Miglyol®812, Miglyol®818, Mazol®, Sefsol®860, Sefsol®870; Miglyol®812 being the most preferred. Miglyol®812 is a fractionated coconut oil comprising caprylic-capric acid triglycerides and having a molecular weight of about 520 Daltons. Fatty acid composition=$C_6$ max. about 3%, $C_8$ about 50 to 65%, $C_{10}$ about 30 to 45%, $C_{12}$ max 5%; acid value about 0.1; saponification value about 330 to 345; iodine value max 1. Miglyol® 812 is available from Condea. Neobee® M 5 F is a fractionated caprylic-capric acid triglyceride available from coconut oil; acid value max. 0.2; saponification value about 335 to 360; iodine value max 0.5, water content max. 0.15%, $D.^{20}$ 0.930-0.960, $n_D^{20}$ 1.448-1.451 (manufacturer information). Neobee® M 5 F is available from Stepan Europe. A further example is Miglyol 829 containing additionally esters with succinic acid.

5) Glyceryl mono-$C_{16}$-$C_{18}$-fatty acid esters

These may be obtained by esterifying glycerol with vegetable oil followed by molecular distillation. Monoglycerides suitable for use in the compositions of the invention include both symmetric (i.e. β-monoglycerides) as well as asymmetric monoglycerides (α-monoglycerides. They also include both uniform glycerides (in which the fatty acid constituent is composed primarily of a single fatty acid) as well as mixed glycerides (i.e. in which the fatty acid constituent is composed of various fatty acids). The fatty acid constituent may include both saturated and unsaturated fatty acids having a chain length of from e.g. $C_{16}$-$C_{18}$. Suitable examples include GMOrphic by Eastman, Rylo MG20 distilled monoglyceride by Danisco Ingredients, or Monomuls 90-O18 by Henkel. For example GMOrphic®-80 (glyceryl monooleate) exhibits the following additional characterising data: monoglyceride content min. 94%, C18:1 content 75% min., peroxide value max. 2.5, C18:2+C18:3 max. 15%, C16:0+C18:0+C20:0 max. 10%, water max. 2%, acid value max. 3, iodine value 65-75, saponification value 155-165, free glycerine max. 1%, hydroxyl number 300-330 (manufacturer information).

6) Mixed mono-, di-, tri-glycerides

These may include mixed mono-, di-, tri-glycerides that are commercially available under the trade name Maisine® from Gattefossé. They are transesterification products of corn oil and glycerol. Such products are comprised predominantly of linoleic and oleic acid mono-, di- and tri-glycerides together with minor amounts of palmitic and stearic acid mono-, di- and tri-glycerides (corn oil itself being comprised of ca. 56% by weight linoleic acid, 30% oleic acid, ca. 10% palmitic and ca. 3% stearic acid constituents). Physical characteristics are: free glycerol max 10%, monoglycerides ca. 40%, diglycerides ca. 40%, triglycerides ca. 10%, free oleic acid content ca. 1%. Further physical characteristics are: acid value max. 2, iodine value of 85-105, saponification value of 150-175, mineral acid content=0. The fatty acid content for Maisine® is typically: palmitic acid ca. 11%, stearic acid ca. 2.5%, oleic acid ca. 29%, linoleic acid ca. 56%, others ca. 1.5% (H. Fiedler, loc. cit., volume 2, page 1079; manufacturer information).

Mixed mono-, di-, tri-glycerides preferably comprise mixtures of $C_8$ to $C_{10}$ or $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. Preferably however they are predominantly comprised of unsaturated fatty acid residues; in particular $C_{18}$ unsaturated fatty acid residues. Suitably the mixed mono-, di-, tri-glycerides comprise at least 60%, preferably at least 75%, more preferably at least 85% by weight of a $C_{18}$ unsaturated fatty acid (for example linolenic, linoleic and oleic acid) mono-, di- and tri-glycerides. Suitably the mixed mono-, di-, tri-glycerides comprise less than 20%, for example about 15% or 10% by weight or less, saturated fatty acid (for example palmitic and stearic acid) mono-, di- and tri-glycerides. Mixed mono-, di-, tri-glycerides are preferably predominantly comprised of mono- and di-glycerides; for example mono- and di-glycerides comprise at least 50%, more preferably at least 70% based on the total weight of the lipophilic phase or component. More preferably, the mono- and di-glycerides comprise at least 75% (for example about 80% or 85% by weight of the lipophilic component. Preferably monoglycerides comprise from about 25 to about 50%, based on the total weight of the lipophilic component, of the mixed mono-, di-, tri-glycerides. More preferably from about 30 to about 40% (for example 35 to 40%) monoglycerides are present. Preferably diglycerides comprise from about 30 to about 60%, based on the total weight of the lipophilic component, of the mixed mono-, di-, tri-glycerides. More preferably from about 40 to about 55% (for example 48 to 50%) diglycerides are present. Triglycerides suitably comprise at least 5% but less than about 25%, based on the total weight of the lipophilic component, of the mixed mono-, di-, tri-glycerides. More preferably from about 7.5 to about 15% (for example from about 9 to 12%) triglycerides are present. Mixed mono-, di-, tri-glycerides may be prepared by admixture of individual mono-, di- or tri-glycerides in appropriate relative proportion. Conveniently however they comprise trans-esterification products of vegetable oils, for example almond oil, ground nut oil, olive oil, peach oil, palm oil or, preferably, corn oil, sunflower oil or safflower oil and most preferably corn oil, with glycerol. Such transesterification products are generally obtained as described in GB 2 257 359 or WO 94/09211. Preferably some of the glycerol is first removed to give a "substantially glycerol free batch" when soft gelatine capsules are to be made. Purified transesterification products of corn oil and glycerol provide particularly suitable mixed mono-, di-, and tri-glycerides hereinafter referred to as "refined oil" and produced according to procedures described in United Kingdom patent specification GB 2,257,359 or international patent publication WO 94/09211.

7) Acetylated monoglycerides (C18)

These may include, for example, Myvacet 9-45.

8) Propylene glycol monofatty acid esters

The fatty acid constituent may include both saturated and unsaturated fatty acids having a chain length of from e.g. $C_8$-$C_{12}$. Particularly suitable are propylene glycol mono ester of caprylic and lauric acid as commercially available, e.g. under the trade names Sefsol® 218, Capryol®90 or Lauroglycol®90, from e.g. Nikko Chemicals Co., Ltd. or Gattefossé or Capmul PG-8 from Abitec Corporation. For example Lauroglycol®90 exhibits the following additional characterising data: acid value max. 8, saponification value 200-220, iodine value max. 5, free propylene glycol content max. 5%, monoester content min. 90% (H. Fiedler, loc. cit., vol 2, page 1025, manufacturer information); Sefsol® 218 exhibits the following additional characterising data: acid value max. 5, hydroxy value 220-280.

9) Propylene glycol mono- and di-fatty acid esters

These may include Laroglycol FCC and Capryol PGMC.

10) Propylene glycol diesters

Propylene glycol di-fatty acid esters such as propylene glycol dicaprylate (which is commercially available under the trade name Miglyol® 840 from e.g. sasol; H. Fiedler, loc. cit., volume 2, page 1130) or Captex 200 from Abitec Corporation.

11) Propylene glycol monoacetate and propylene glycol diacetate

12) Transesterified ethoxylated vegetable oils

These may include transesterified ethoxylated vegetable oils such as those obtained by reacting various natural vegetable oils (for example, corn oil, maize oil, castor oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst. These procedures are described in United States patent specification U.S. Pat. No. 3,288,824. Transesterified ethoxylated corn oil is particularly preferred.

Transesterified ethoxylated vegetable oils are known and are commercially available under the trade name Labrafil® (H. Fiedler, loc. cit., vol 2, page 994). Examples are Labrafil® M 2125 CS (obtained from corn oil and having an acid value of less than about 2, a saponification value of 155 to 175, an HLB value of 3 to 4, and an iodine value of 90 to 110), and Labrafil® M 1944 CS (obtained from kernel oil and having an acid value of about 2, a saponification value of 145 to 175 and an iodine value of 60 to 90). Labrafil® M 2130 CS (which is a transesterification product of a $C_{12-18}$ glyceride and polyethylene glycol and which has a melting point of about 35 to 40° C., an acid value of less than about 2, a saponification value of 185 to 200 and an iodine value of less than about 3) may also be used. The preferred transesterified ethoxylated vegetable oil is Labrafil® M 2125 CS which can be obtained, for example, from Gattefossé, Saint-Priest Cedex, France.

13) Sorbitan fatty acid esters

Such esters may include e.g. sorbitan mono $C_{12-18}$ fatty acid esters, or sorbitan tri $C_{12-18}$ fatty acid esters are commercially available under the trade mark Span® from e.g. uniqema. An especially preferred product of this class is e.g. Span® 20 (sorbitan monolaurate) or Span® 80 (sorbitan monooleate) (Fiedler, loc. cit., 2, p. 1571; Handbook of Pharmaceutical Excipients, loc. cit., page 511).

14) Esterified compounds of fatty acid and primary alcohols

These may include esterified compounds of fatty acid having 8 to 20 carbon atoms and primary alcohol having 2 to 3 carbon atoms, for example, isopropyl myristate, isopropyl palmitate, ethyl linoleate, ethyl oleate, ethylmyristate etc., with an esterified compound of linoleic acid and ethanol being particularly preferable, also isopropylmyristat and isopropylpalmitat.

15) Glycerol triacetate or (1,2,3)-triacetin

May be obtained by esterifying glycerin with acetic anhydride. Glycerol triacetate is commercially available as, e.g. Priacetin® 1580 from Unichema International, or as Eastman™ Triacetin from Eastman, or from Courtaulds Chemicals Ltd. Glycerol triacetate exhibits the following additional characterising data: molecular weight 218.03, $D.^{20,3}$ 1.159-1.163, $n_D^{20}$ 1.430-1.434, water content max. 0.2%, viscosity (25°) 17.4 mPa s, acid value max. 0.1, saponification value of about 766-774, triacetin content 97% min. (H. Fiedler, loc. cit. vol 2, page 1720; Handbook of Pharmaceutical Excipients, loc. cit., page 534, manufacturer information).

16) Acetyl triethyl citrate

This may be obtained by esterification of citric acid and ethanol, followed by acetylation with acetic anhydride, respectively. Acetyl triethyl citrate is commercially available, e.g. under the trade name Citroflex® A-2, from e.g. Morflex Inc.

17) Tributylcitrate or acetyl tributyl citrate

18) Polyglycerol fatty acid esters

These have for example from 2 to 10, e.g. 6 glycerol units. The fatty acid constituent can include both saturated and unsaturated fatty acids having a chain length of from e.g. $C_8$-$C_{18}$. Particularly suitable is e.g. Plurol Oleique CC497 from Gattefossé, having a saponification value of 133-155 and a saponification value of 196-244. Further suitable polyglycerol fatty acid esters include diglyceryl monooleate (DGMO) and Hexaglyn-5-O, as known and commercially available from e.g. Nikko Chemicals Co., Ltd.

19) PEG-fatty alcohol ether

This may include Brij 30™ polyoxyethylene(4) lauryl ether.

20) Fatty alcohols and fatty acids

Fatty acids may be obtained by hydrolysing various animal and vegetable fats or oils, such as olive oil, followed by separation of the liquid acids. The fatty acid/alcohol constituent can include both saturated and mono- or di-unsaturated fatty acids/alcohols having a chain length of from e.g. $C_6$-$C_{20}$. Particularly suitable are, e.g. oleic acid, oleyl alcohol, linoleic acid, capric acid, caprylic acid, caproic acid, tetradecanol, dodecanol, or decanol. Oleyl alcohol is commercially available under the trade mark HD-Eutanol® V from e.g. Henkel KGaA. Oleyl alcohol exhibits the following additional characterising data: acid value max 0.1, hydroxy value of about 210, iodine value of about 95, saponification value max 1, $D.^{20}$ about 0.849, $n_C^{20}$ 1.462, molecular weight 268, viscosity (20°) about 35 mPa s (manufacturer information). Oleic acid exhibits the following additional characterising data: molecular weight 282.47, $D.^{20}$ 0.895, $n_D^{20}$ 1.45823, acid value 195-202, iodine value 85-95, viscosity (25°) 26 mPa s (H. Fiedler, loc. cit., volume 2, page 1236; "Handbook of Pharmaceutical Excipients", 2nd Edition, Editors A. Wade and P. J. Weller (1994), Joint publication of American Pharmaceutical Assoc., Washington, USA and The Pharmaceutical Press, London, England, page 325).

21) Tocopherol and its derivatives (e.g. acetate)

These may include Coviox T-70, Copherol 1250, Copherol F-1300, Covitol 1360 and Covitol 1100.

22) Pharmaceutically acceptable oils

Alternatively, the lipophilic component comprises e.g. a pharmaceutically acceptable oil, preferably with an unsaturated component such as a vegetable oil.

23) Alkylene polyol ethers or esters

These may include $C_{3-5}$alkylene triols, in particular glycerol, ethers or esters. Suitable $C_{3-5}$alkylene triol ethers or esters include mixed ethers or esters, i.e. components including other ether or ester ingredients, for example transesterification products of $C_{3-5}$alkylene triol esters with other mono-, di- or poly-ols. Particularly suitable alkylene polyol ethers or esters are mixed $C_{3-5}$alkylene triol/poly-($C_{2-4}$alkylene) glycol fatty acid esters, especially mixed glycerol/polyethylene- or polypropylene-glycol fatty acid esters.

Especially suitable alkylene polyol ethers or esters include products obtainable by transesterification of glycerides, e.g. triglycerides, with poly-($C_{2-4}$alkylene) glycols, e.g. poly-ethylene glycols and, optionally, glycerol. Such transesterification products are generally obtained by alcoholysis of glycerides, e.g. triglycerides, in the presence of a poly-($C_{2-4}$alkylene) glycol, e.g. polyethylene glycol and, optionally, glycerol (i.e. to effect transesterification from the glyceride to the poly-alkylene glycol/glycerol component, i.e. via polyalkylene glycolysis/glycerolysis).

In general such reaction is effected by reacting the indicated components (glyceride, polyalkylene glycol and, optionally, glycerol) at elevated temperature under an inert atmosphere with continuous agitation.

Preferred glycerides are fatty acid triglycerides, e.g. ($C_{10-22}$ fatty acid) triglycerides, including natural and hydrogenated oils, in particular vegetable oils. Suitable vegetable oils include, for example, olive, almond, peanut, coconut, palm, soybean and wheat germ oils and, in particular, natural or hydrogenated oils rich in ($C_{12-18}$ fatty acid) ester residues. Preferred polyalkylene glycol materials are polyethylene glycols, in particular polyethylene glycols having a molecular weight of from ca. 500 to ca. 4,000, e.g. from ca. 1,000 to ca. 2,000.

Suitable alkylene polyol ethers or esters include mixtures of $C_{3-5}$alkylene triol esters, e.g. mono-, di- and tri-esters in variable relative amount, and poly ($C_{2-4}$alkylene) glycol mono- and di-esters, together with minor amounts of free $C_{3-5}$alkylene triol and free poly-($C_{2-5}$ alkylene) glycol. As hereinabove set forth, the preferred alkylene triol moiety is glyceryl; preferred polyalkylene glycol moieties include polyethylene glycol, in particular having a molecular weight of from ca. 500 to ca. 4,000; and preferred fatty acid moieties will be $C_{10-22}$fatty acid ester residues, in particular saturated $C_{10-22}$fatty acid ester residues.

Particularly suitable alkylene polyol ethers or esters include transesterification products of a natural or hydrogenated vegetable oil and a polyethylene glycol and, optionally, glycerol; or compositions comprising or consisting of glyceryl mono-, di- and tri-$C_{10-22}$fatty acid esters and polyethylene glycol mono- and di-$C_{10-22}$ fatty esters (optionally together with, e.g. minor amounts of free glycerol and free polyethylene glycol).

Preferred vegetable oils, polyethylene glycols or polyethylene glycol moieties and fatty acid moieties in relation to the above definitions are as hereinbefore set forth.

Particularly suitable alkylene polyol ethers or esters as described above for use in the present invention include those commercially available under the trade name Gelucire® from e.g. Gattefossé, in particular the products:

a) Gelucire® 33/01, which has an m.p.=ca. 33-37° C. and a saponification value of ca. 230-255;
b) Gelucire® 39/01, m.p.=ca. 37.5-41.5° C., saponification v.=ca. 225-245;
c) Gelucire® 43/01, m.p.=ca. 42-46° C., saponification v.=ca. 220-240;

Products (a) to (c) above all have an acid value of maximum of 3. The compositions of the invention may include mixtures of such ethers or esters.

24) Hydrocarbons
These may include e.g. squalene, available from e.g. Nikko Chemicals Co., Ltd.

25) Ethylene glycol esters
These may include Monthyle® (ethylene glycol monostearate), available from e.g. Gattefossé.

26) Pentaerythriol fatty acid esters and polyalkylene glycol ethers
These may include, for example pentaerythrite-dioleate, -distearate, -monolaurate, -polyglycol ether, and -monostearate as well as pentaerythrite-fatty acid esters (Fiedler, loc. cit., 2, p. 1288-1290, incorporated herein by reference).

Some of the lipophilic components, e.g. (1-3, 5-6, 8-9, 12-13, 19), display surfactant-like behaviour and may also be termed co-surfactants.

The lipophilic component preferably comprises 5 to 85% by weight of the composition of the invention, e.g. 10 to 85%; preferably 15 to 60% by weight, more preferably about 15 to about 40% by weight.

The compositions of the present invention preferably contain one or more surfactants to reduce the interfacial tension thereby providing thermodynamic stability.

Surfactants may be complex mixtures containing side products or unreacted starting products involved in the preparation thereof, e.g. surfactants made by polyoxyethylation may contain another side product, e.g. polyethylene glycol. The complex mixtures or each surfactant preferably has a hydrophilic-lipophilic balance (HLB) value of 8 to 17, especially 10 to 17. The HLB value is preferably the mean HLB value.

Suitable surfactants include:

1) Reaction products of a natural or hydrogenated castor oil and ethylene oxide
The natural or hydrogenated castor oil may be reacted with ethylene oxide in a molar ratio of from about 1:35 to about 1:60, with optional removal of the polyethylene-glycol component from the products. Various such surfactants are commercially available. Particularly suitable surfactants include polyethyleneglycol-hydrogenated castor oils available under the trade name Cremophor®; Cremophor® RH 40, which has a saponification value of about 50 to 60, an acid value less than about 1, a water content (Fischer) less than about 2%, an $n_D^{60}$ of about 1.453-1.457 and an HLB of about 14-16; and Cremophor® RH 60, which has a saponification value of about 40-50, an acid value less than about 1, an iodine value of less than about 1, a water content (Fischer) of about 4.5-5.5%, an $n_D^{60}$ of about 1.453-1.457 and an HLB of about 15 to 17.

An especially preferred product of this class is Cremophor® RH40. Other useful products of this class are available under the trade names Nikkol® (e.g. Nikkol® HCO-40 and HCO-60), Mapeg® (e.g. Mapeg® CO-40h), Incrocas® (e.g. Incrocas® 40), Tagat® (for example polyoxyethylene-glycerol-fatty acid esters e.g. Tagat® RH 40) and Simulsol OL-50 (PEG-40 castor oil, which has a saponification value of about 55 to 65, an acid value of max. 2, an iodine value of 25 to 35, a water content of max. 8%, and an HLB of about 13, available from Seppic). These surfactants are further described in Fiedler loc. cit.

Other suitable surfactants of this class include polyethyleneglycol castor oils such as that available under the trade name Cremophor® EL, which has a molecular weight (by steam osmometry) of about 1630, a saponification value of about 65 to 70, an acid value of about 2, an iodine value of about 28 to 32 and an $n_D^{25}$ of about 1.471.

2) Polyoxyethylene-sorbitan-fatty acid esters

These may include mono- and tri-lauryl, palmityl, stearyl and oleyl esters of the type known and commercially available under the trade name Tween® (Fiedler, loc. cit. p. 1754 ff) from Uniqema including the products: Tween® 20 [polyoxyethylene(20)sorbitanmonolaurate], Tween® 21 [polyoxyethylene(4)sorbitanmonolaurate], Tween® 40 [polyoxyethylene(20)sorbitanmonopalmitate], Tween® 60 [polyoxyethylene(20)sorbitanmonostearate], Tween® 65 [polyoxyethylene(20)sorbitantristearate], Tween® 80 [polyoxyethylene(20)sorbitanmonooleate], Tween® 81 [polyoxyethylene(5)sorbitanmonooleate], and Tween® 85 [polyoxyethylene(20)sorbitantrioleate]. Especially preferred products of this class are Tween® 20 and Tween® 80.

3) Polyoxyethylene fatty acid esters

These may include polyoxyethylene stearic acid esters of the type known and commercially available under the trade name Myrj® from Uniqema (Fiedler, loc. cit., 2, p. 1166). An especially preferred product of this class is Myrj® 52 having a $D^{25}$ of about 1.1., a melting point of about 40 to 44° C., an HLB value of about 16.9., an acid value of about 0 to 1 and a saponification no. of about 25 to 35.

4) Polyoxyethylene-polyoxypropylene co-polymers and block co-polymers or poloxamers These may include the type known and commercially available under the trade names Pluronic® and Emkalyx® (Fiedler, loc. cit., 2, p. 1329). An especially preferred product of this class is Pluronic® F68 (poloxamer 188) from BASF, having a melting point of about 52° C. and a molecular weight of about 6800 to 8975. A further preferred product of this class is Synperonic® PE L44 (poloxamer 124) from Uniqema.

5) Polyoxyethylene mono esters of a saturated $C_{10}$ to $C_{22}$

These may include $C_{18}$ substituted e.g. hydroxy fatty acid; e.g. 12 hydroxy stearic acid PEG ester, e.g. of PEG about e.g. 600-900 e.g. 660 Daltons MW, e.g. Solutol® HS 15 from BASF, Ludwigshafen, Germany. According to the BASF technical leaflet MEF 151E (1986) comprises about 70% polyethoxylated 12-hydroxystearate by weight and about 30% by weight unesterified polyethylene glycol component. Solutol HS 15 has a hydrogenation value of 90 to 110, a saponification value of 53 to 63, an acid number of maximum 1, and a maximum water content of 0.5% by weight.

6) Polyoxyethylene alkyl ethers

These may include polyoxyethylene glycol ethers of $C_{12}$ to $C_{18}$ alcohols, e.g. Polyoxyl 2-, 10- or 20-cetyl ether or Polyoxyl 23-lauryl ether, or polyoxyl 20-oleyl ether, or Polyoxyl 2-, 10-, 20- or 100-stearyl ether, as known and commercially available e.g. under the trade mark Brij® from Uniqema. An especially preferred product of this class is e.g. Brij® 35 (Polyoxyl 23 lauryl ether) or Brij® 98 (Polyoxyl 20 oleyl ether) (Fiedler, loc. cit., 1, pp. 259; Handbook of Pharmaceutical Excipients, loc. cit., page 367). Similarly suitable products include polyoxyethylene-polyoxypropylene-alkyl ethers, e.g. polyoxyethylene-polyoxypropylene-ethers of $C_{12}$ to $C_{18}$ alcohols, e.g. polyoxyethylen-20-polyoxypropylene-4-cetylether which is known and commercially available under the trade mark Nikko PBC® 34, from e.g. Nikko Chemicals Co., Ltd. (Fiedler, loc. cit., vol. 2, pp. 1210). Polyoxypropylene fatty acid ethers, e.g. Acconon® E are also suitable.

7) Sodium alkyl sulfates and sulfonates, and sodium alkyl aryl sulfonates

These may include sodium lauryl sulfate, which is also known as sodium dodecyl sulfate and commercially available, e.g. under the trade name Texapon K12® from Henkel KGaA.

8) Water soluble tocopheryl polyethylene glycol succinic acid esters (TPGS)

These may include those with a polymerisation number ca 1000, e.g. available from Eastman Fine Chemicals Kingsport, Tex., USA, or available from Cognis.

9) PoIN/glycerol fatty acid esters

These may include those with e.g. from 10 to 20, e.g. 10 glycerol units. The fatty acid constituent may include both saturated and unsaturated fatty acids having a chain length of from e.g. $C_8$-$C_{18}$. Particularly suitable is e.g. decaglycerylmonolaurat or decaglycerylmonomyristat, as known and commercially available under the trade mark Decaglyn® 1-L or Decaglyn® 1-M or Decaglyn 1-O, respectively, from e.g. Nikko Chemicals C., Ltd (Fiedler, loc. cit., vol. 2, pp. 1359).

10) Alkylene polyol ethers or esters

These may include $C_{3-5}$alkylene triols, in particular glycerol, ethers or esters. Suitable $C_{3-5}$alkylene triol ethers or esters include mixed ethers or esters, i.e. components including other ether or ester ingredients, for example transesterification products of $C_{3-5}$alkylene triol esters with other mono-, di- or poly-ols. Particularly suitable alkylene polyol ethers or esters are mixed $C_{3-5}$alkylene triol/poly-($C_{2-4}$alkylene) glycol fatty acid esters, especially mixed glycerol/polyethylene- or polypropylene-glycol fatty acid esters.

Especially suitable alkylene polyol ethers or esters include products obtainable by transesterification of glycerides, e.g. triglycerides, with poly-($C_{2-4}$alkylene) glycols, e.g. poly-ethylene glycols and, optionally, glycerol.

Such transesterification products are generally obtained by alcoholysis of glycerides, e.g. triglycerides, in the presence of a poly-($C_{2-4}$alkylene) glycol, e.g. polyethylene glycol and, optionally, glycerol (i.e. to effect transesterification from the glyceride to the poly-alkylene glycol/glycerol component, i.e. via poly-alkylene glycolysis/gly-cerolysis). In general such reaction is effected by reacting the indicated components (glyceride, polyalkylene glycol and, optionally, glycerol) at elevated temperature under an inert atmosphere with continuous agitation.

Preferred glycerides are fatty acid triglycerides, e.g. ($C_{10-22}$fatty acid) triglycerides, including natural and hydrogenated oils, in particular vegetable oils. Suitable vegetable oils include, for example, olive, almond, peanut, coconut, palm, soybean and wheat germ oils and, in particular, natural or hydrogenated oils rich in ($C_{12-18}$fatty acid) ester residues.

Preferred polyalkylene glycol materials are polyethylene glycols, in particular polyethylene glycols having a molecular weight of from ca. 500 to ca. 4,000, e.g. from ca. 1,000 to ca. 2,000.

Suitable alkylene polyol ethers or esters include mixtures of $C_{3-5}$alkylene triol esters, e.g. mono-, di- and tri-esters in variable relative amount, and poly ($C_{2-4}$alkylene) glycol mono- and di-esters, together with minor amounts of free $C_{3-5}$alkylene triol and free poly- ($C_{2-5}$alkylene) glycol. As hereinabove set forth, the preferred alkylene triol moiety is glyceryl; preferred polyalkylene glycol moieties include polyethylene glycol, in particular having a molecular weight of from ca. 500 to ca. 4,000; and preferred fatty acid moieties will be $C_{10-22}$ fatty acid ester residues, in particular saturated $C_{10-22}$ fatty acid ester residues.

Particularly suitable alkylene polyol ethers or esters include transesterification products of a natural or hydrogenated vegetable oil and a polyethylene glycol and, optionally, glycerol; or compositions comprising or consisting of glyceryl mono-, di- and tri-$C_{10-22}$fatty acid esters and polyethylene glycol mono- and di-$C_{10-22}$fatty esters (optionally together with, e.g. minor amounts of free glycerol and free polyethylene glycol).

Preferred vegetable oils, polyethylene glycols or polyethylene glycol moieties and fatty acid moieties in relation to the above definitions are as hereinbefore set forth.

Particularly suitable alkylene polyol ethers or esters as described above for use in the present invention include those commercially available under the trade name Gelucire® from e.g. Gattefossé, in particular the products:

a) Gelucire® 44/14, m.p.=ca. 42.5-47.5° C., saponification v.=ca. 79-93;
b) Gelucire® 50/13, m.p.=ca. 46-51° C., saponification v.=ca. 67-81;

Products (a) to (b) above all have an acid value of maximum of 2.

Alkylene polyol ethers or esters having an iodine value of maximum 2 are generally preferred. The compositions of the invention may include mixtures of such ethers or esters.

Gelucire® products are inert semi-solid waxy materials with amphiphilic character. They are identified by their melting point and their HLB value. Most Gelucire® grades are saturated polyglycolised glycerides obtainable by polyglycolysis of natural hydro-genated vegetable oils with polyethylene glycols. They are composed of a mixture of mono-, di- and tri-glycerides and mono- and di-fatty acid esters of polyethylene glycol. Particularly suitable is Gelucire® 44/14 which has a nominal melting point of 44° C. and an HLB of 14. It is obtained by reacting hydrogenated palm kernels and/or hydrogenated palm oils with polyethylene glycol 1500. It consists of approximately 20% mono-, di- and triglycerides, 72% mono- and di-fatty acid esters of polyethylene glycol 1500 and 8% of free polyethylene glycol 1500. The fatty acid distribution for Gelucire® 44/14 is as follows: 4-10 $C_8$, 3-9 $C_{10}$, 40-50 $C_{12}$, 14-24 $C_{14}$, 4-14 $C_{16}$, 5-15 $C_{18}$. Gelucire® 44/14 exhibits the following additional characterising data: acid value of max. 2, iodine value of max. 2, saponification value of 79-93, hydroxyl value of 36-56, peroxide value of max. 6, alkaline impurities max. 80, water content max. 0.50, free glycerol content max. 3, monoglycerides content 3.0-8.0. (H. Fiedler, loc. cit., vol page 773; manufacturer information).

11) Polyethylene glycol glyceryl fatty acid esters

The fatty acid ester may include mono and/or di and/or tri fatty acid ester. The fatty acid constituent may include both saturated and unsaturated fatty acids having a chain length of from e.g. $C_{12}$-$C_{18}$. The polyethylene glycols may have e.g. from 10 to 40 [$CH_2$—$CH_2$—O] units, e.g. 15 or 30 units. Particularly suitable is polyethylene glycol (15) glyceryl monostearat which is commercially available, e.g. under the trade name TGMS®-15, e.g. from Nikko Chemicals Co., Ltd. Other suitable glyceryl fatty acid esters include polyethylene glycol (30) glyceryl monooleate which is commercially available, e.g. under the trade name Tagat® 0, e.g. from Goldschmidt (H. Fiedler, loc. cit., vol. 2, p. 1502-1503), and Tagat 02 (polytheylene glycol (20) glycerol monooleate, as well as Tagat L (polytheylene glycol (30) glycerol monolaurate) and Tagat L2 (polytheylene glycol (20) glycerol monolaurate), all e.g. from Goldschmidt (H. Fiedler, loc. cit., vol. 2, p. 1650). A further suitable polyethylene glycol glyceryl fatty acid ester is Tagat TO.

12) Sterols and derivatives thereof

These may include cholesterols and derivatives thereof, in particular phytosterols, e.g. products comprising sitosterol, campesterol or stigmasterol, and ethylene oxide adducts thereof, for example soya sterols and derivatives thereof, e.g. polyethylene glycol sterols, e.g. polyethylene glycol phytosterols or polyethylene glycol soya sterols. The polyethylene glycols may have e.g. from 10 to 40 [$CH_2$—$CH_2$—O] units, e.g. 25 or 30 units. Particularly suitable is polyethylene glycol (30) phytosterol which is commercially available, e.g. under the trade name Nikko BPS®-30, e.g. from Nikko Chemicals Co., Ltd. Further suitable is polyethylene glycol (25) soya sterol which is commercially available, e.g. under the trade name Generol® 122 E 25, e.g. from Henkel (H. Fiedler, loc. cit., vol. 1, p. 779).

13) Transesterified, polyoxyethylated caprylic-capric acid glycerides

These may include those that are commercially available under the trade name Labrasol® from e.g. Gattefossé. Labrasol® has an acid value of max. 1, a saponification value of 90-110, and an iodine value of max. 1 (H. Fiedler, loc. cit., vol 2, page 995).

14) Sugar fatty acid esters

These may include those of $C_{12}$-$C_{18}$ fatty acids, e.g. sucrose monolaurate, e.g. Ryoto L-1695®, which is commercially available from e.g. Mitsubishi-Kasei Food Corp., Tokyo, Japan.

15) PEG sterol ethers

These may include those having, e.g. from 5 to 35 [$CH_2$—$CH_2$—O] units, e.g. 20 to 30 units, e.g. Solulan® C24, which is commercially available from e.g. Amerchol.

16) Dioctylsodiumsulfosuccinate

This is commercially available under the trade mark Aerosol OT® from e.g. American Cyanamid Co. (Fiedler, loc. cit., 1, p. 164), or di-[2-ethylhexyl]-succinate (Fiedler, loc. cit., volume 1, p. 574).

17) Phospholipids

These may include, in particular, lecithins (Fiedler, loc. cit., volume 2, p. 910, 1030). Suitable lecithins include, in particular, soya bean lecithins.

18) Salts of fatty acids, fatty acid sulfates and sulfonates

These may include those of e.g. $C_6$-$C_{18}$, fatty acids, -fatty acid sulfates and sulfonates, as known and commercially available from e.g. Fluka.

19) Salts of acylated amino acids

These may include those of $C_6$-$C_{18}$, acylated amino acids, e.g. sodium lauroyl sarcosinate, which is commercially available from e.g. Fluka.

20) Medium or long-chain alkyl, e.g. $C_6$-$C_{18}$, ammonium salts

These may include $C_6$-$C_{18}$ acylated amino acids e.g. cetyl trimethyl ammonium bromide, which is commercially available from e.g. E. Merck AG.

The surfactant may comprise 5 to 90% by weight of the composition of the invention; preferably 10 to 85% by weight, more preferably 15 to 60% by weight.

It will be appreciated that some surfactants may also act as hydrophilic component and some hydrophilic components may also act as surfactants.

Certain embodiments of the compositions of the invention include additives for example antioxidants, antimicrobial agents, enzyme inhibitors, stabilizers, preservatives, flavours, sweeteners and other components such as those described in Fiedler, H. P., loc. cit.

These additives or ingredients may comprise about 0.05 to 5% by weight of the total weight of the composition. Antimicrobial agents, enzyme inhibitors, stabilizers or preservatives typically provide up to about 0.05 to 1% by weight based on the total weight of the composition. Sweetening or flavouring agents typically provide up to about 2.5 or 5% by weight based on the total weight of the composition.

In another aspect, the invention provides a process for preparing a dispersible, preferably spontaneously dispersible, pharmaceutical composition containing alisporivir, which process comprises bringing alisporivir and a carrier medium comprising (1) a lipophilic component, (2) a surfactant, (3) a hydrophilic component, and (4) water into intimate admixture.

The carrier medium can be prepared separately before bringing the active agent into intimate admixture with the carrier medium. Alternatively, the two or more of the components of the carrier medium can be mixed together with the active agent.

The spontaneously dispersible or dispersible pharmaceutical composition is preferably a preconcentrate, such as lipid-/surfactant-based formulation as herein defined.

The spontaneously dispersible or dispersible pharmaceutical compositions preferably spontaneously or substantially spontaneously form an o/w (oil-in-water) micro-/emulsion, when diluted with an aqueous medium such as water to a dilution of 1:1 to 1:300, e.g. 1:1 to 1:70, especially 1:10 to 1:70, more especially e.g. 1:10, or in the gastric juices of a patient after oral administration/application.

In another aspect, the invention provides a process for preparing a pharmaceutical composition containing alisporivir, which process comprises:
(i) bringing alisporivir and a carrier comprising (1) a lipophilic component, (2) a surfactant, (3) a hydrophilic component, and (4) water into intimate admixture to form a spontaneously dispersible or dispersible pharmaceutical composition;
The above process my optionally further comprise the step of
(ii) diluting the spontaneously dispersible or dispersible pharmaceutical composition in an aqueous medium to form a micro-/emulsion.

As mentioned above, the active agent, in particular, alisporivir, may be present in an amount by weight of up to about 30% by weight of the composition, e.g. about 20% by weight. The active agent is preferably present in an amount of about 15 to about 25% by weight of the composition, more preferably, in an amount of about 15% to about 20% by weight of the composition.

The hydrophilic component may comprise about 5% to about 45% by weight of the composition of the invention, e.g. about 5% to about 40%; preferably about 5% to about 30% by weight, more preferably about 10% to about 25% by weight.

The composition of the invention preferably contains from about 5% to about 45% of a hydrophilic component by weight. Thus, a particularly suitable composition contains hydrophilic component from about 5% to about 45% by weight of e.g. ethanol, polyethyleneglycol 400, or triethylcitrate diethylene glycol monoethyl ether or propylene glycol.

The lipophilic component preferably comprises about 5% to about 45% by weight of the composition of the invention, e.g. about 10% to about 35%; preferably about 15% to about 20% by weight.

The composition of the invention preferably contains from about 5% to about 45% of a lipophilic component by weight. Thus, a particularly suitable composition contains as lipophilic component from about 5% to about 45% by weight of e.g. medium chain triglycerides, corn oil mono-di-triglycerides, sorbitan monooleate, linoleoyl macrogolglycerides or oleic acid.

The surfactant may comprise about 5% to about 70% by weight of the composition of the invention; preferably about 20% to about 45% by weight, more preferably about 20% to about 40% by weight.

The composition of the invention preferably contains from about 5% to about 70% of a surfactant by weight. Thus, a particularly suitable composition contains as surfactant from about 5% to about 45% by weight. Suitable surfactants include, for instance, Macrogolglycerol hydroxystearate, Caprylocaproyl Macrogol-8 glycerides, Vitamin E Polyethylene Glycol Succinate or Glyceryl caprylate.

The water may be present in an amount of about 2% to about 15% by weight of the composition of the invention, preferably about 3% to about 10% by weight, more preferably about 4% to about 5% by weight, e.g. about 5% by weight.

The relative proportion of the active agent(s), the lipophilic component(s), the surfactant(s) the hydrophilic component(s), and water preferably may result in a colloidal system that lies within the "emulsion" region on a standard three way plot graph. The compositions will therefore be of high stability and are capable, on addition to an aqueous medium, of becoming emulsions.

In another aspect, the present invention provides a pharmaceutical composition, preferably in the form of a lipid-/surfactant-based formulation for oral administration comprising:
1) alisporivir in an amount of about 15% to about 20% by weight of the composition;
2) a lipophilic component, wherein the lipophilic component is in an amount from about 5 to about 45% by weight, preferably about 15% to about 20% by weight and wherein the lipophilic component is selected from the group consisting of medium chain triglycerides, corn oil mono-di-triglycerides, sorbitan monooleate, linoleoyl macrogolglycerides and oleic acid;
3) a surfactant;
4) a hydrophilic component;
5) water in an amount of about 2% to about 10% by weight of the composition.

In another aspect, the present invention provides a pharmaceutical composition, preferably in form of a lipid-/surfactant-based formulation for oral administration comprising:
1) alisporivir in an amount of about 15% to about 20% by weight of the composition;
2) a lipophilic component, wherein the lipophilic component is in an amount from about 5% to about 45% by weight, preferably about 15% to about 20% by weight and wherein the lipophilic component is selected from the group consisting of medium chain triglycerides, corn oil mono-di-triglycerides, sorbitan monooleate, linoleoyl macrogolglycerides and oleic acid;
3) a surfactant, wherein the surfactant is in an amount from about 5% to about 45% by weight and wherein the surfactant is selected from the group consisting of Macrogolglycerol hydroxystearate, Caprylocaproyl Macrogol-8 glycerides, Vitamin E Polyethylene Glycol Succinate and Glyceryl caprylate;
4) a hydrophilic component;
5) water in an amount of about 2% to about 10% by weight of the composition.

In another aspect, the present invention provides a pharmaceutical composition, preferably in form of a lipid-/surfactant-based formulation for oral administration comprising:
1) alisporivir in an amount of about 15% to about 20% by weight of the composition;
2) a lipophilic component, wherein the lipophilic component is in an amount from about 5% to about 45% by weight, preferably about 15% to about 20% by weight and wherein the lipophilic component is selected from the group consisting of medium chain triglycerides, corn oil mono-di-triglycerides, sorbitan monooleate, linoleoyl macrogolglycerides and oleic acid;
3) a surfactant, wherein the surfactant is in an amount from about 5% to about 45% by weight and wherein the surfactant is selected from the group consisting of Macrogolglycerol hydroxystearate, Caprylocaproyl Macrogol-8 glycerides, Vitamin E Polyethylene Glycol Succinate and Glyceryl caprylate;
4) a hydrophilic component wherein the hydrophilic component is in an amount from about 5% to about 45% by weight, about 5% to about 30% by weight, more preferably about 10% to about 25% by weight and wherein the hydrophilic component is selected from the group consisting of ethanol, polyethyleneglycol, triethylcitrate, diethylene glycol monoethyl ether and propylene glycol;
5) water in an amount of about 2% to about 10% by weight of the composition.

In another aspect, the present invention provides a pharmaceutical composition, preferably in form of a lipid-/surfactant-based formulation for oral administration comprising:
1) alisporivir in an amount of about 15% to about 20% by weight of the composition;
2) a lipophilic component, wherein the lipophilic component is in an amount from about 5% to about 45% by weight, preferably about 15% to about 20% by weight and wherein the lipophilic component is selected from the group consisting of medium chain triglycerides, corn oil mono-di-triglycerides, sorbitan monooleate, linoleoyl macrogolglycerides and oleic acid;
3) a surfactant, wherein the surfactant is in an amount from about 5% to about 45% by weight and wherein the surfactant is selected from the group consisting of Macrogolglycerol hydroxystearate, Caprylocaproyl Macrogol-8 glycerides, Vitamin E Polyethylene Glycol Succinate and Glyceryl caprylate;
4) a hydrophilic component wherein the hydrophilic component is in an amount from about 5% to about 45% by weight, about 5% to about 30% by weight, more preferably about 10% to about 25% by weight and wherein the hydrophilic component is selected from the group consisting of ethanol, polyethyleneglycol, triethylcitrate, diethylene glycol monoethyl ether and propylene glycol;
5) water in an amount of about 3% to about 6% by weight of the composition, preferably of about 4% to about 5% by weight of the composition;
optionally comprising a co-surfactant other than ethanol, preferably glycerol in an amount of about up to 5% by weight of the composition, preferably of about 1.5% to about 4% by weight of the composition.

In another aspect, the present invention provides a pharmaceutical composition, preferably in form of a lipid-/surfactant-based formulation for oral administration comprising:
1) alisporivir in an amount of about 15% to about 20% by weight of the composition;
2) a lipophilic component, wherein the lipophilic component is selected from the group consisting of medium chain triglycerides, corn oil mono-di-triglycerides, sorbitan monooleate, linoleoyl macrogolglycerides and oleic acid;
3) a surfactant, wherein the surfactant selected from the group consisting of Macrogolglycerol hydroxystearate, Caprylocaproyl Macrogol-8 glycerides, Vitamin E Polyethylene Glycol Succinate and Glyceryl caprylate;
4) a hydrophilic component wherein the hydrophilic component is selected from the group consisting of ethanol and polyethyleneglycol;
5) water in an amount of about 2% to about 10% by weight of the composition.

In preferred embodiment, the present invention provides a pharmaceutical composition, preferably in form of a lipid-/surfactant-based formulation for oral administration comprising:
1) alisporivir in an amount of about 19% to about 20% by weight of the composition;
2) a lipophilic component, wherein the lipophilic component is selected from the group consisting of medium chain triglycerides and sorbitan monooleate, in an amount from about 5% to about 45% by weight, preferably about 15% by weight;
3) a surfactant, wherein the surfactant selected from the group consisting of Caprylocaproyl Macrogol-8 glycerides and Vitamin E Polyethylene Glycol Succinate and in an amount from about 5 to about 45%, preferably about 40% by weight;
4) a hydrophilic component wherein the hydrophilic component is selected from the group consisting of ethanol and polyethyleneglycol, in an amount from about 10% to about 25% by weight, preferably about 20% by weight;
5) water in an amount of about 2% to about 10% by weight of the composition.

The active ingredient may be present in an amount by weight of the composition of about 15% to about 30%; for example, in an amount by weight of about 15% to about 20%, 19% to about 20%, for example 15%, 16%, 17%, 18%, 19%, or 20%.

In another aspect, the present invention provides a pharmaceutical composition, preferably in form of a lipid-/surfactant-based formulation for oral administration comprising alisporivir in an amount of about 5% to about 15% by weight of the composition for example, in an amount by weight of about 5% to about 10%, for example about 5%, about 6%, about 7%, about 8%, about 9%, or about 10%.

In another aspect, the present invention provides a pharmaceutical composition, preferably in form of a lipid-/ surfactant-based formulation for oral administration comprising alisporivir in an amount of about 5% to about 15% by weight of the composition; and a hydrophilic component wherein the hydrophilic component is in an amount from about 5 to about 45% by weight, about 5% to about 30% by weight, more preferably about 10% to about 25% by weight and wherein the hydrophilic component is selected from the group consisting of ethanol, polyethyleneglycol, triethylcitrate, diethylene glycol monoethyl ether and propylene glycol; and wherein when alisporivir is in an amount of 10% and the hydrophilic component is ethanol or propylene glycol, the composition does not contain 41% of polyethyleneglycol-hydrogenated castor oil.

In another aspect, the present invention provides a pharmaceutical composition, preferably in form of a lipid-/surfactant-based formulation for oral administration comprising:
1) alisporivir in an amount of about 5% to about 15% by weight of the composition;
2) a lipophilic component, wherein the lipophilic component is in an amount from about 5 to about 45% by weight, preferably about 15% to about 20% by weight and wherein the lipophilic component is selected from the group consisting of medium chain triglycerides, corn oil mono-di-triglycerides, sorbitan monooleate, linoleoyl macrogolglycerides and oleic acid;
3) a surfactant, wherein the surfactant is in an amount from about 5 to about 45% by weight and wherein the surfactant is selected from the group consisting of Macrogolglycerol hydroxystearate, Caprylocaproyl Macrogol-8 glycerides, Vitamin E Polyethylene Glycol Succinate and Glyceryl caprylate;
4) a hydrophilic component wherein the hydrophilic component is in an amount from about 5 to about 45% by weight, about 5% to about 30% by weight, more preferably about 10% to about 25% by weight and wherein the hydrophilic component is selected from the group consisting of ethanol, polyethyleneglycol, triethylcitrate, diethylene glycol monoethyl ether and propylene glycol.

When the composition of the invention as defined above is a microemulsion preconcentrate it may be combined with water or an aqueous solvent medium to form a micro-/emulsion. The emulsion or microemulsion may be administered enterally, for example orally, for example in the form of a capsule or a drinkable solution which can be taken orally and swallowed.

When the composition of the invention is a preconcentrate, such as lipid-/surfactant-based formulation, a unit dosage of the preconcentrate formulation is preferably used to fill orally administrable capsule shells. The capsule shells may be soft or hard capsule shells, for example made of gelatine. Each unit dosage will suitably contain from about 0.1 to about 200 mg active agent, for example about 0.1 mg, about 0.25 mg, about 0.5 mg, about 1 mg, about 2 mg, about 10 mg, about 15 mg, about 25 mg, about 50 mg, about 75 mg, about 100 mg, about 150 mg or about 200 mg of the active agent. Such unit dosage forms are suitable for administration 1 to 5 times daily depending upon the particular purpose of therapy, the phase of therapy and the like.

The compositions, as defined above, may be in drink solution form and may include water or any other aqueous system, e.g. fruit juice, milk, and the like, to provide e.g. colloidal systems, suitable for drinking, e.g. with a dilution of from about 1:10 to about 1:100.

The pharmaceutical compositions of the invention may exhibit especially advantageous properties when administered orally; for example, in terms of consistency and high level of bioavailability obtained in standard bioavailability trials. Such trials are performed in animals, e.g. rats or dogs or healthy volunteers using chromatographic methods, e.g. HPLC.

The compositions of the invention, e.g. those in the examples hereinafter, may show good stability characteristics as indicated by standard stability trials, for example having a shelf life stability of up to one, two or three years, and even longer. One group of compositions of the invention may be of high stability that are capable, on addition to water, of providing aqueous emulsions.

The compositions of the invention exhibit especially advantageous properties when administered orally; for example, in terms of consistency and high levels of bioavailability obtained in standard bioavailability trials.

Pharmacokinetic parameters, for example drug substance absorption and measured for example as blood levels, also become surprisingly more predictable and problems in administration with erratic absorption may be eliminated or reduced. Additionally the pharmaceutical compositions are effective with biosurfactants or tenside materials, for example bile salts, being present in the gastro-intestinal tract. That is, the pharmaceutical compositions of the present invention are fully dispersible in aqueous systems comprising such natural tensides and thus capable of providing emulsion or microemulsion systems and/or particulate systems in situ which are stable. The function of the pharmaceutical compositions upon oral administration remain substantially independent of and/or unimpaired by the relative presence or absence of bile salts at any particular time or for any given individual. The compositions of this invention may also reduce variability in inter- and intra-patient dose response.

The optimal dosage of active agent to be administered to a particular patient must be considered carefully. It may be advisable to monitor the blood serum levels of the active agent by radioimmunoassay, monoclonal antibody assay, or other appropriate conventional means. Dosages of alisporivir will generally range from about 100 to about 1600 mg per day, e.g. about 200 mg to about 1200 mg per day for a 75 kilogram adult, preferably about 400 mg to about 1200 mg, with the optimal dosage being approximately about 800 to about 1200 mg per day.

The pharmaceutical compositions as defined herein are preferably compounded in unit dosage form, for example, by filling them into orally administrable capsule shells. The capsule shells may be soft or hard gelatin or HPMC-based (Hydroxypropylmethyl cellulose) capsule shells such as Vegicaps.® Where the pharmaceutical composition is in unit dosage form, each unit dosage will suitably contain between about 50 and about 400 mg of the active agent; for example, about 50 mg, about 100 mg, about 200 mg, about 300 mg, about 400 mg. Such unit dosage forms are suitable for administration once or more times daily depending upon the particular purpose of therapy, the phase of therapy and the like.

In another aspect, the present invention provides a pharmaceutical composition, preferably in form of a lipid-/surfactant-based formulation for oral administration as defined above, for use as a medicament, preferably in treatment of a Hepatitis C virus infected patient and wherein alisporivir is to be administered in an amount of about 400 to about 600 mg twice per day.

In another aspect, the present invention provides a pharmaceutical composition, preferably in form of a lipid-/surfactant-based formulation for oral administration as defined above, for use as a medicament, preferably in treatment of a Hepatitis C virus infected patient and wherein (i) alisporivir is administered during an initial phase in an amount of about 600 mg, twice per day; (ii) followed by administering alisporivir during the second phase in an amount of 600 mg or about 800 mg once per day.

As used herein, the term "about", unless the context dictates otherwise, is used to mean a range of + or −10%.

As used herein, the term "by weight", unless the context dictates otherwise, is used to mean by weight of the composition, e.g. percentage by weight of the composition. As used herein, the term "by weight" in the context of mixtures such as mixtures of hydrophilic components, of lipophilic components, or of surfactants, unless the context dictates otherwise, is used to mean the sum of the weights of the respective components of the mixture by weight of the composition.

In another aspect, the present invention provides a method of treatment of a subject suffering from a disorder treatable with alisporivir comprising administering a therapeutically effective amount of a pharmaceutical composition of the invention to a subject in need of such treatment.

In a further aspect, the present invention provides the use of alisporivir for the manufacture of a pharmaceutical composition for the treatment of a subject suffering from a disorder treatable with alisporivir.

The utility of all the pharmaceutical compositions of the present invention may be observed in standard clinical tests in, for example, known indications of active agent dosages giving equivalent blood levels of active agent; for example using dosages in the range of 100 mg to 1200 mg of active agent per day for a 75 kilogram mammal, e.g. adult and in standard animal models. The increased bioavailability of the active agent provided by the compositions may be observed in standard animal tests and in clinical trials, e.g. as described above.

The pharmaceutical compositions of the present invention are particularly useful for treatment and prevention Hepatitis C virus infections or HCV induced disorders in a patient, multiple sclerosis, muscular dystrophy, Ullrich congenital muscular dystrophy and ischemia.

The following non-limiting examples illustrate further aspects of the invention and are preferred embodiments of the invention.

Example 1

This Example (and Examples 2 through 3) describes means to prepare high drug load alisporivir (DEB025) (≥19 wt %) lipid-based formulations and illustrates means to increase the equilibrium solubility of DEB025 ethanol solvate above the target drug load of such formulations through the addition of water.

A stock solution of the DEB025 formulations shown in Table 1 (Formulations A1 to A3) and Table 2 (Formulations A through C) was prepared as follows. Solid or semi-solid excipients were heated in a water bath at 50° C. and well stirred prior dispensing step. A quantity of each excipient was weighted into a glass bottle, followed by addition of ethanol. The excipients were stirred at room temperature until a homogeneous solution was obtained. Then, an adequate amount of DEB025 amorphous form was added to the glass bottle containing the prepared vehicle and stirred with magnetic bar at room temperature until complete dissolution of drug substance (clear light yellow solution with no visible drug particles). The stock solution was then aliquoted into small glass vials (2 g) followed by the addition of a small amount of DEB025 ethanol solvate (60 to 120 mg). For formulations comprising no ethanol, the amorphous form of DEB025 was added to the vials. Vials were placed at 25° C. and stirred with magnetic bar until an excess of solid drug identified as DEB025 ethanol solvate or DEB025 amorphous form (for ethanol-free compositions) was obtained (at least 24 h). An additional amount of DEB025 ethanol solvate or DEB025 amorphous form (60 to 120 mg) was added to those vials showing a clear solution upon equilibration. These vials were re-equilibrated until an excess of drug was observed. Finally, the supernatant from these suspensions was filtrated and analyzed for DEB025 using HPLC.

TABLE 1

Compositions of DEB025 vitamin E TPGS-based formulations and corresponding equilibrium solubility of DEB025/DEB025 ethanol solvate at room temperature (21 ± 2° C.).

| | | % (w/w) | | |
| --- | --- | --- | --- | --- |
| Component | Function | Formulation A1 | Formulation A2 | Formulation A3 |
| DEB025 | Active substance | 20.0 | 20.0 | 20.0 |
| Ethanol Anhydrous | Hydrophilic solvent | 20.0 | 10.0 | 5.0 |
| Carprylocaproyl Macrogol-8 glycerides (Labrasol) | Surfactant | 25.0 | 29.2 | 31.3 |
| Vitamin E Polyethylene Glycol Succinate (TPGS) | Surfactant | 15.0 | 17.5 | 18.7 |
| Medium chain triglycerides (Miglyoil 812) | Oily solubilizer | 5.0 | 5.8 | 6.3 |
| Sorbitan oleate (Span 80) | Oily solubilizer | 15.0 | 17.5 | 18.7 |
| Equilibrium solubility at 21 ± 2° C. (wt %)[1] | | 10.4 ± 0.14 | 7.07 ± 0.11 | 6.99 ± 0.10 |

[1]Average ± standard deviation (n = 2)

TABLE 2

Compositions of DEB025 vitamin E TPGS-based formulations and equilibrium solubility of DEB025 ethanol solvate measured at 25° C.

| | | % (w/w) | | |
|---|---|---|---|---|
| Component | Function | Formulation A | Formulation B | Formulation C |
| DEB025 | Active substance | 19.5 | 19.0 | 18.5 |
| Ethanol Anhydrous | Hydrophilic solvent | 22.0 | 24.0 | 26.0 |
| Caprylocaproyl Macrogol-8 glycerides (Labrasol) | Surfactant | 24.4 | 23.8 | 23.1 |
| Vitamin E Polyethylene Glycol Succinate (TPGS) | Surfactant | 14.6 | 14.3 | 13.9 |
| Medium chain triglycerides (Miglyol 812) | Oily solubilizer | 4.9 | 4.8 | 4.6 |
| Sorbitan oleate (Span 80) | Oily solubilizer | 14.6 | 14.3 | 13.9 |
| Equilibrium solubility at 25° C. (wt %)[1] | | 11.6 ± 0.1 | 12.5 ± 0.4 | 14.1 ± 0.9 |

[1]Average ± standard deviation (n = 2)

Figure 2:
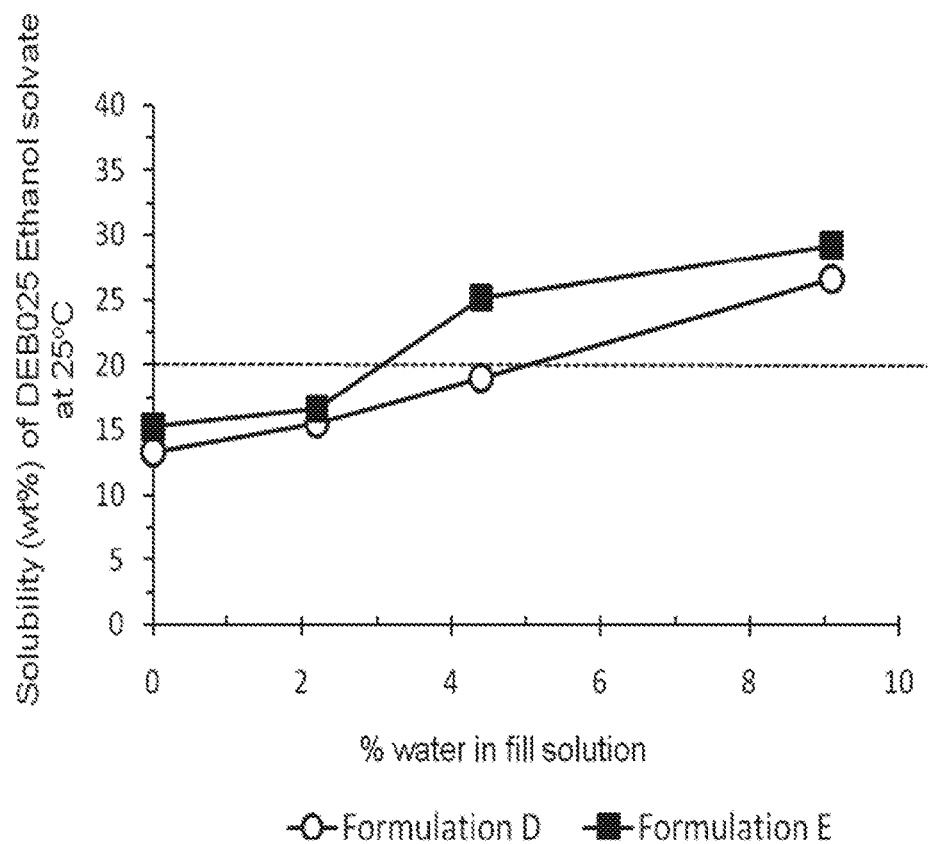
FIG. 2 is a graph which illustrates the impact of water in the equilibrium solubility at 25° C. of DEB025 Ethanol solvate in Cremophor RH40-based formulations.

The impact of water on the equilibrium solubility of DEB025 ethanol solvate was evaluated by adding water at the concentrations as indicated in FIG. 1 to 2 g aliquots of the stock solutions listed in Table 2. A small amount of DEB025 ethanol solvate (ca. 10 mg) was then added to the vial, and equilibrium solubility of DEB025 ethanol solvate was measured at 25° C. as described above.

Example 2

DEB025 (amorphous form) was formulated with the compositions listed in Table 3 (formulations D1, D and E), and the equilibrium solubility of DEB025 ethanol solvate was measured at 25° C. as a function of water (FIG. 2). The formulations and solubility measurements were done as described in Example 1.

TABLE 3

Compositions of DEB025 Cremophor RH40-based formulations and equilibrium solubility of DEB025 ethanol solvate measured at 25° C.

| | | % (w/w) | | |
|---|---|---|---|---|
| Component | Function | Formulation D1 | Formulation D | Formulation E |
| DEB025 | Active substance | 10.0 | 19.0 | 19.0 |
| Ethanol Anhydrous | Hydrophilic solvent | 10.0 | 19.0 | 23.8 |
| Macrogolglycerol hydroxystearate (Cremophor RH40) | Surfactant | 40.0 | 30.7 | 28.0 |
| Corn oil glycerides | Oily solubilizer | 32.0 | 24.6 | 22.4 |
| Propylene glycol | Hydrophilic solvent | 8.0 | 6.7 | 6.8 |
| Equilibrium solubility at 25° C. (wt %) | | 7.3 | 13.3 | 15.2 |

Example 3

Figure 3:
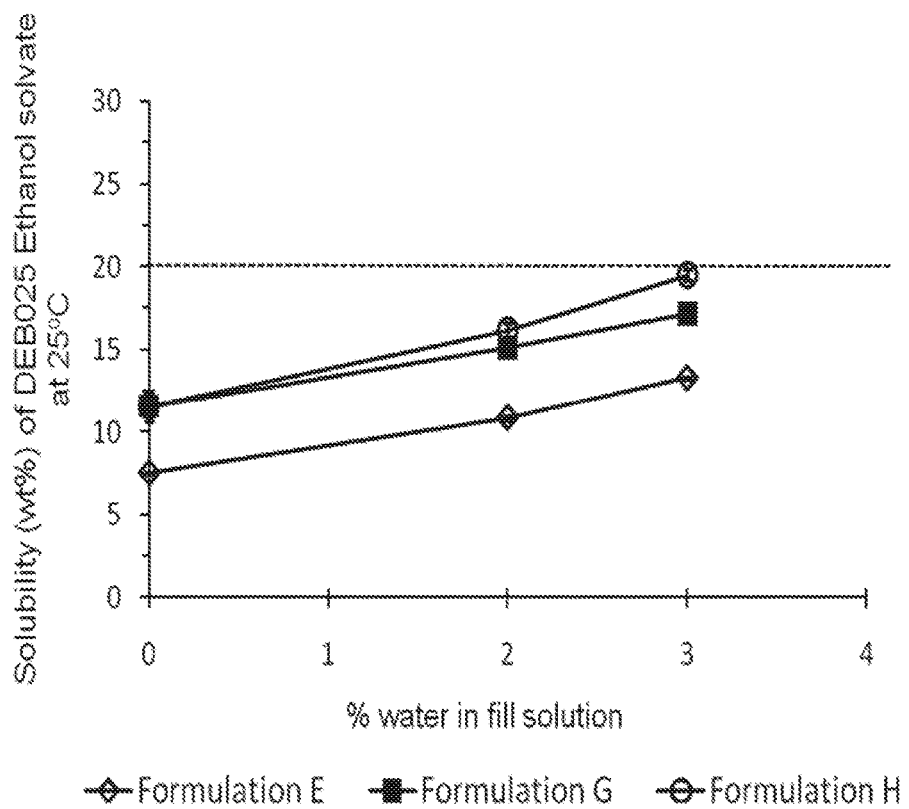
FIG. 3 is a graph which illustrates the impact of water in the equilibrium solubility at 25° C. of DEB025 Ethanol solvate in PEG400-based formulations.

DEB025 (amorphous form) was formulated with the compositions listed in Table 4 (formulations F through H), and the equilibrium solubility of DEB025 ethanol solvate was measured at 25° C. as a function of water (FIG. 3). The formulations and solubility measurements were done as described in Example 1.

TABLE 4

Compositions of DEB025 formulations containing PEG400 and equilibrium solubility of DEB025 ethanol solvate measured at 25° C.

| | | % (w/w) | | |
|---|---|---|---|---|
| Component | Function | Formulation F | Formulation G | Formulation H |
| DEB025 | Active substance | 19.4 | 19.2 | 19.0 |
| Ethanol Anhydrous | Hydrophilic solvent | 12.6 | 18.5 | 24.1 |
| Polyethylene glycol 400 (PEG400) | Hydrophilic solvent | 9.7 | 4.8 | 9.5 |

TABLE 4-continued

Compositions of DEB025 formulations containing PEG400 and equilibrium solubility of DEB025 ethanol solvate measured at 25° C.

|  |  | % (w/w) | | |
|---|---|---|---|---|
| Component | Function | Formulation F | Formulation G | Formulation H |
| Carprylocaproyl Macrogol-8 glycerides (Labrasol) | Surfactant | 24.3 | 24.0 | 19.7 |
| Vitamin E Polyethylene Glycol Succinate (TPGS) | Surfactant | 14.6 | 14.4 | 11.9 |
| Medium chain triglycerides (Miglyoil 812) | Oily solubilizer | 4.9 | 4.8 | 4.0 |
| Sorbitan oleate (Span 80) | Oily solubilizer | 14.6 | 14.4 | 11.9 |
| Equilibrium solubility at 25° C. (wt %)[1] |  | 7.5 ± 0.1 | 11.6 ± 1.2 | 11.5 ± 0.2 |

[1]Average ± standard deviation (n = 3)

Example 4

This Example (and Example 5) illustrates formulations of DEB025 intended for encapsulation in 200 mg soft-gelatin capsules. Fill solution formulations were prepared as described in Example 1. Equilibrium solubility of DEB025 ethanol solvate in fill solution mimicking the final capsule was measured at 20° C. in the presence of water and glycerol (common plasticizer used in manufacture of soft-gelatin capsules) at the final concentrations (wt %) listed in Table 5.

TABLE 5

Compositions of 200 mg DEB025 soft-gelatin formulations and equilibrium solubility of DEB025 ethanol solvate measured at 20° C.

|  | mg/SGC | | |
|---|---|---|---|
| Component | Formulation I (18.9 wt % DEB025) | Formulation J (18.9 wt % DEB025) | Formulation K (15.4 wt % DEB025) |
| DEB025 | 200.0 | 200.0 | 200.0 |
| Ethanol Anhydrous | 200.0 | 200.0 | 240.0 |
| Carprylocaproyl Macrogol-8 glycerides (Labrasol) | 250.0 | 250.0 | 316.7 |
| Vitamin E Polyethylene Glycol Succinate (TPGS) | 150.0 | 150.0 | 190.0 |
| Medium chain triglycerides (Miglyoil 812) | 50.0 | 50.0 | 63.3 |
| Sorbitan oleate (Span 80) | 150.0 | 150.0 | 190 |
| Capsule fill weight | 1060 | 1060 | 1300 |
| Water content (wt %) | 3.0 | 5.0 | 3.5 |
| Glycerol content (wt %) | 3.4 | 3.0 | 4 |
| Equilibrium solubility at 20° C. (wt %)[1] | 16.8 ± 1.1 | 21.1 ± 0.2 | 17.1 ± 0.8 |

[1]Average ± standard deviation (n = 3 to 6)

Example 5

This Example illustrates high drug load formulations of DEB025 (19 wt %) containing PEG400 intended for encapsulation in 200 mg soft-gelatin capsules. Fill solution formulations were prepared as described in Example 1. Equilibrium solubility of DEB025 ethanol solvate in fill solution mimicking the final capsule was measured at 20° C. as described in Example 4.

TABLE 6

Compositions of 200 mg DEB025 soft-gelatin formulations with PEG400 and equilibrium solubility of DEB025 ethanol solvate measured at 20° C.

|  | % (w/w) | | |
|---|---|---|---|
| Component | Formulation L | Formulation M | Formulation N |
| DEB025 | 200 | 200 | 200 |
| Ethanol Anhydrous | 100 | 150 | 200 |
| Polyethylene glycol 400 (PEG400) | 100 | 50 | 100 |
| Carprylocaproyl Macrogol-8 glycerides (Labrasol) | 250 | 250 | 208 |
| Vitamin E Polyethylene Glycol Succinate (TPGS) | 150 | 150 | 125 |
| Medium chain triglycerides (Miglyoil 812) | 50 | 50 | 42 |
| Sorbitan oleate (Span 80) | 150 | 150 | 125 |
| Target capsule fill weight | 1060 | 1060 | 1060 |
| Water content (wt %) | 5.0 | 5.0 | 5.0 |
| Glycerol content (wt %) | 3.0 | 3.0 | 3.0 |
| Equilibrium solubility at 20° C. (wt %) | 25.3 ± 0.2[1] | 25.9 ± 0.4[2] | 22.4 ± 1.7[2] |

[1]Average ± standard deviation (n = 3);
[2]n = 2

Example 6

This Example illustrates formulations of DEB025 with reduced ethanol content (≤5) intended for either encapsulation in soft gelatin capsules or filling into bottles (Tables 6 through 8). Fill solution formulations were prepared as described in Example 1. Equilibrium solubility of DEB025 ethanol solvate or amorphous DEB025 (for ethanol-free formulations) were measured in the formulation at 21±2° C. as described in Example 1.

TABLE 6

Compositions of DEB025 formulations with reduced ethanol content (5%) and saturation solubility at room temperature (21 ± 2° C.)

|  |  | % (w/w) | | |
|---|---|---|---|---|
| Component | Function | Formulation O | Formulation P | Formulation Q |
| DEB025 | Active substance | 5.0 | 7.0 | 5.0 |

TABLE 6-continued

Compositions of DEB025 formulations with reduced ethanol content (5%) and saturation solubility at room temperature (21 ± 2° C.)

| Component | Function | % (w/w) Formulation O | Formulation P | Formulation Q |
|---|---|---|---|---|
| Ethanol Anhydrous | Hydrophilic solvent | 5.0 | 5.0 | 5.0 |
| Macrogolglycerol hydroxystearate (Cremophor RH40) | Surfactant | 36.0 | 34.4 | 45.0 |
| Corn oil glycerides | Oily solubilizer | 27.0 | 25.8 | 27.0 |
| Polyethylene glycol 400 (PEG400) | Hydrophilic solvent | 27.0 | 25.8 | 18.0 |
| Water | Hydrophilic solvent | — | 2.0 | — |
| Equilibrium solubility at 21 ± 2° C. (wt %)[1] | | 6.73 ± 0.01 | 8.0 ± 0.3 | 6.0 ± 0.3 |

[1]Average ± standard deviation (n = 2);

TABLE 7

Compositions of DEB025 formulations with reduced ethanol content (≤5%) and saturation solubility at room temperature (21 ± 2° C.)

| Component | Function | % (w/w) Formulation R | Formulation S | Formulation T | Formulation U |
|---|---|---|---|---|---|
| DEB025 | Active substance | 5.0 | 5.0 | 5.0 | 5.0 |
| Ethanol Anhydrous | Hydrophilic solvent | 5.0 | 5.0 | — | — |
| Polyoxyethylene (80) sorbitan mono oleate (Tween 80) | Surfactant | 54.0 | 54.0 | 57.0 | 57.0 |
| Medium chain triglycerides (Miglyoil 812) | Oily solubilizer | 18.0 | — | 19.0 | — |
| Linoleoyl macrogolglyceride (Labrafil M2125 CS) | Oily solubilizer | — | 9.0 | — | 9.5 |
| Polyethylene glycol 400 (PEG400) | Hydrophilic solvent | 18.0 | 27.0 | 19.0 | 28.5 |
| Equilibrium solubility at 21 ± 2° C. (wt %)[1] | | 6.5 ± 0.01 | 5.9 ± 0.01 | <10 | 5.7 ± 5.0 |

[1]Average ± standard deviation (n = 2)

TABLE 8

Compositions of DEB025 formulations with reduced ethanol content (≤5%) and saturation solubility at room temperature (21 ± 2° C.)

| Component | Function | % (w/w) Formulation V | Formulation X |
|---|---|---|---|
| DEB025 | Active substance | 10.0 | 18.0 |
| Ethanol Anhydrous | Hydrophilic solvent | 5.0 | 5.0 |
| Macrogolglycerol hydroxystearate (Cremophor RH40) | Surfactant | 34.0 | 30.8 |
| Glyceryl Caprylate/ Caprate Mono-/di-glycerides (Capmul MCMC8) | Oily solubilizer | 34.0 | 38.5 |
| Polyethylene glycol 400 (PEG400) | Hydrophilic solvent | 17.0 | 7.7 |
| Equilibrium solubility at 21 ± 2° C. (wt %)[1] | | 11.7 ± 0.2 | 19.5 ± 0.3 |

[1]Average ± standard deviation (n = 2)

Example 7

This Example presents formulations comprising about 20% DEB025 and which are intended as solution (Formulation O), as intermediate for encapsulation in soft gelatin capsules (Formulation P), as final composition in soft gelatin capsules (Formulation Q).

The manufacturing process of the fill for 10 g of 20% formulations DEB025 (Formulation O) has been made as following:

Dissolve 2 g Debio 025 in 2 g ethanol, put it in an ultrasonic bath until complete dissolution.

Add 2.5 g Macrogol glycerolcaprylocaprate (Labrasol®).

Add 0.5 g Triglycerides Medium Chain (Labrafac® WL1349).

Add 1.5 g Sorbitan oleate (Montane® 80).

Add 1.5 g Alpha tocopherol PEG succinate previously heated (TPGS)

Mix it by hand or with a vortex during approximately 30 s.

TABLE 9

Compositions of DEB025 formulations as a liquid solution, a process intermediate before encapsulation and after encapsulation

| Component | Formulation O (g) | Formulation P (g) | Formulation Q (mg of fill per capsule) |
|---|---|---|---|
| DEB025 | 2.0 | 2.0 | 200.0 |
| Ethanol 96% (Ph Eur) | 2.0 | 2.6 | 200.0 |
| Carprylocaproyl Macrogol-8 glycerides (Labrasol) | 2.5 | 2.5 | 250.0 |
| Vitamin E Polyethylene Glycol Succinate (TPGS) | 1.5 | 1.5 | 150.0 |
| Medium chain triglycerides (Labrafac WL1349) | 0.5 | 0.5 | 50.0 |
| Sorbitan oleate (Span 80) | 1.5 | 1.5 | 150.0 |
| Sub-total | 10.0 | 10.0 | n.a. |
| Capsule fill | n.a. | n.a. | 1000.0 |
| Theoretical water content (wt %) | >0.8% | >1.04% | >2% |
| Glycerol content (wt %) | n.a. | n.a. | 8.43% |

For formulation O, after dilution of 200 mg oin 200 mL water dropplets size of are stable for 2 hours (t0 308 nm PI 0.08, t2h: 291 nm PI 0.06). Apparatus Zetasizer 3000.

Example 8

This Examples illustrate formulations of 10% and 30% DEB025 described as liquid solutions. (Formulation R and S),

TABLE 10

Compositions of DEB025 formulations as a 10% and 30% DEB025 liquid solution

| Component | Formulation R (g) | Formulation S (g) |
|---|---|---|
| DEB025 | 1.0 | 3.0 |
| Ethanol 96% (Ph Eur) | 1.0 | 2.5 |
| Carprylocaproyl Macrogol-8 glycerides (Labrasol) | 3.0 | 2.0 |
| Vitamin E Polyethylene Glycol Succinate (TPGS) | 2.0 | 1.0 |
| Medium chain triglycerides (Labrafac WL1349) | 1.0 | 0.5 |
| Sorbitan oleate (Span 80) | 2.0 | 1.0 |
| Sub-total | 10.0 | 10.0 |
| Water content (wt %) | >0.4% | >1.2% |
| Glycerol content (wt %) | n.a. | n.a. |

Example 9

This Example illustrates the impact of Water, Glycerol, and Ethanol and their possible interactions on the equilibrium solubility of DEB025 ethanol solvate in Formulation A1 (composition listed in Example 1) at 20° C.

Figure 4:
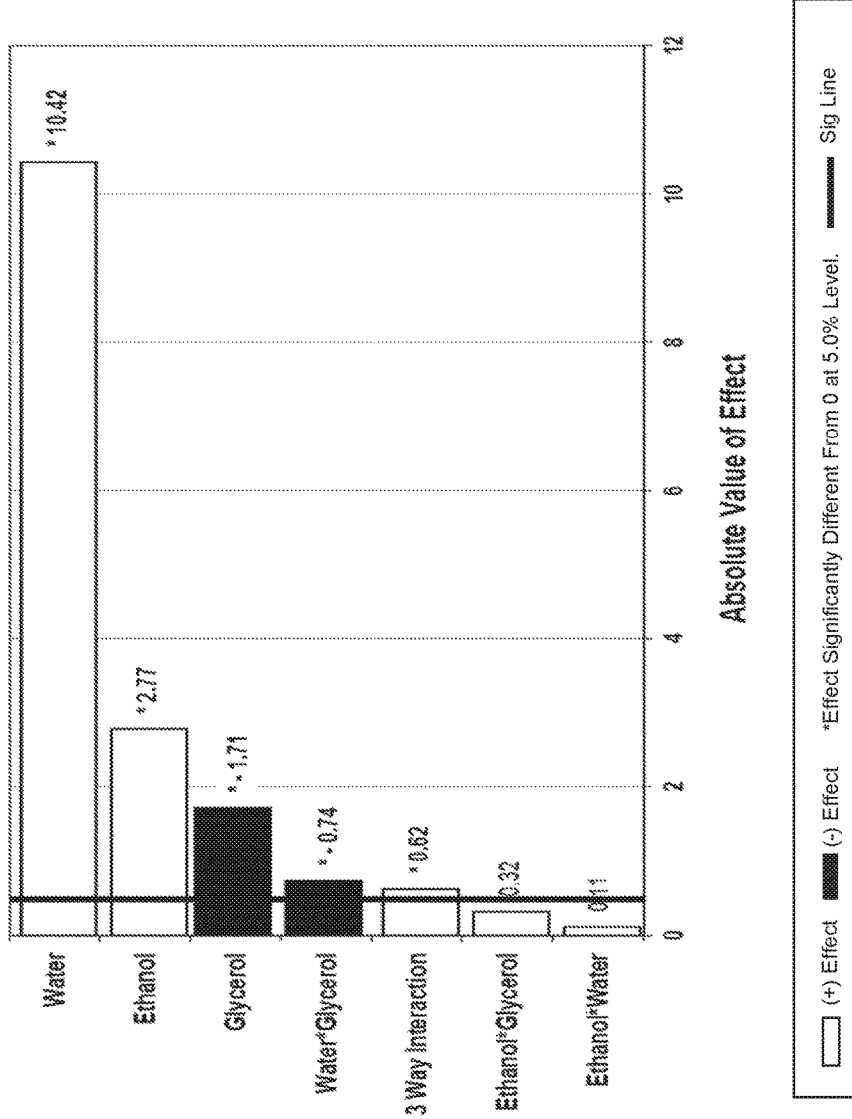
FIG. 4 shows the impact of water, ethanol, and glycerol and their interactions in the equilibrium solubility at 20° C. of DEB025 Ethanol solvate in formulation A1.

A $2^3$ full factorial Design of Experiments (DoE) was performed consisting of 3 variables (Water, Glycerol, and Ethanol), tested at 2 levels each (high and low), with 4 points used as center points, in a total of 12 runs. Table 9 lists the levels for each parameter tested in the DoE and FIG. 4 shows the corresponding Pareto chart of effects for mean solubility.

TABLE 11

Parameter levels tested in DoE

| Parameter (variable) | Paremeter level (wt %) | | |
|---|---|---|---|
| | Low | Center | High |
| Ethanol Anhydrous | 17 | 20 | 23 |
| Water | 3 | 6.5 | 10 |
| Glycerol | 1.5 | 2.75 | 4.0 |

The invention claimed is:

1. A capsule for oral administration comprising a pharmaceutical composition comprising:
   (i) alisporivir in an amount of about 15% to about 20% by weight of the composition,
   (ii) water in an amount of about 2% to about 10% by weight of the composition and a carrier medium comprising
   (iii) a lipophilic component;
   (iv) a surfactant; and
   (v) a hydrophilic component comprising ethanol, wherein ethanol is present in an amount of about 10 to about 25% by weight of the composition.

2. A capsule for oral administration comprising the pharmaceutical composition according to claim 1 wherein the water is in an amount of about 4% to about 5% by weight of the composition.

3. A capsule for oral administration comprising the pharmaceutical composition according to claim 1 wherein the water is in an amount of about 3% to about 6% by weight of the composition.

4. A capsule for oral administration comprising a composition according to claim 1 wherein alisporivir is in an amount of about 19% to about 20% by weight of the composition.

5. A capsule for oral administration comprising a composition according to claim 1 wherein the hydrophilic component further comprises a component selected from the group consisting of polyethyleneglycol, triethylcitrate, diethylene glycol monoethyl ether and propylene glycol.

6. A capsule for oral administration comprising a composition according to claim 1 wherein the lipophilic component is selected from the group consisting of medium chain triglycerides, corn oil mono-di-triglycerides, sorbitan monooleate, linoeoyl macrogolglycerides and oleic acid.

7. A capsule for oral administration comprising a composition according to claim 1 wherein the surfactant is selected from the group consisting of Macrogolglycerol hydroxystearate, Caprylocaproyl Macrogol-8 glycerides, Vitamin E Polyethylene Glycol Succinate and Glyceryl caprylate.

8. A capsule for oral administration comprising the composition according to claim 1 which contains from about 50 to about 400 mg alisporivir.

9. A capsule for oral administration according to claim 1 wherein the capsule is a soft gelatin capsule, a hard gelatin capsule or a HPMC-based capsule.

10. The HPMC-based capsule of claim 9 which is a VEGICAP®.

* * * * *